(12) United States Patent
Im et al.

(10) Patent No.: US 11,744,090 B2
(45) Date of Patent: Aug. 29, 2023

(54) SELF-POWERED PEROVSKITE X-RAY DETECTOR

(71) Applicant: Korea University Research and Business Foundation, Seoul (KR)

(72) Inventors: Sang Hyuk Im, Hwaseong-si (KR); Jin Hyuck Heo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 11 days.

(21) Appl. No.: 17/629,508

(22) PCT Filed: Jul. 23, 2020

(86) PCT No.: PCT/KR2020/009739
§ 371 (c)(1),
(2) Date: Jan. 24, 2022

(87) PCT Pub. No.: WO2021/015578
PCT Pub. Date: Jan. 28, 2021

(65) Prior Publication Data
US 2022/0246873 A1    Aug. 4, 2022

(30) Foreign Application Priority Data

Jul. 23, 2019 (KR) .......................... 10-2019-0088845

(51) Int. Cl.
*G01T 1/20* (2006.01)
*H10K 30/80* (2023.01)
*G01T 1/202* (2006.01)

(52) U.S. Cl.
CPC ............. *H10K 30/80* (2023.02); *G01T 1/202* (2013.01); *G01T 1/2006* (2013.01)

(58) Field of Classification Search
CPC ....... H10K 30/80; G01T 1/2006; G01T 1/202; G01T 1/20; G01T 1/026; G01T 1/1612; G01T 1/24; C01P 2002/34; C01P 2004/04; C01P 2004/64; C01G 21/006; H01L 27/14601; H01L 27/14658; A61B 6/4233; A61B 6/42
See application file for complete search history.

(56) References Cited

U.S. PATENT DOCUMENTS

2019/0162865 A1    5/2019  Huang et al.

FOREIGN PATENT DOCUMENTS

| JP | 2005-003444 A | | 1/2005 |
|---|---|---|---|
| JP | 2005003444 A | * | 1/2005 |

(Continued)

*Primary Examiner* — Kiho Kim
(74) *Attorney, Agent, or Firm* — NSIP Law

(57) ABSTRACT

Disclosed is a self-powered perovskite X-ray detector. The self-powered perovskite X-ray detector according to an embodiment of the present invention has a shape wherein a scintillator converting incident X-rays into visible light is combined with a perovskite photodetector, wherein the scintillator and the perovskite light absorption layer include a perovskite compound represented by Formula 1 below:

$$A_a M_b X_c \qquad \text{[Formula 1]}$$

where A is a monovalent cation, M is a divalent metal cation or a trivalent metal cation, X is a monovalent anion, a+2b=c when M is a divalent metal cation, a+3b=4c when M is a trivalent metal cation, and a, b, and c are natural numbers.

17 Claims, 17 Drawing Sheets

(56) References Cited

FOREIGN PATENT DOCUMENTS

| KR | 10-2017-0112563 A | 10/2017 |
|----|-------------------|---------|
| KR | 10-2018-0024947 A | 3/2018  |
| KR | 10-1839696 B1     | 3/2018  |
| KR | 10-2018-0106851 A | 10/2018 |
| KR | 10-2019-0046820 A | 5/2019  |

\* cited by examiner

[FIG. 1]
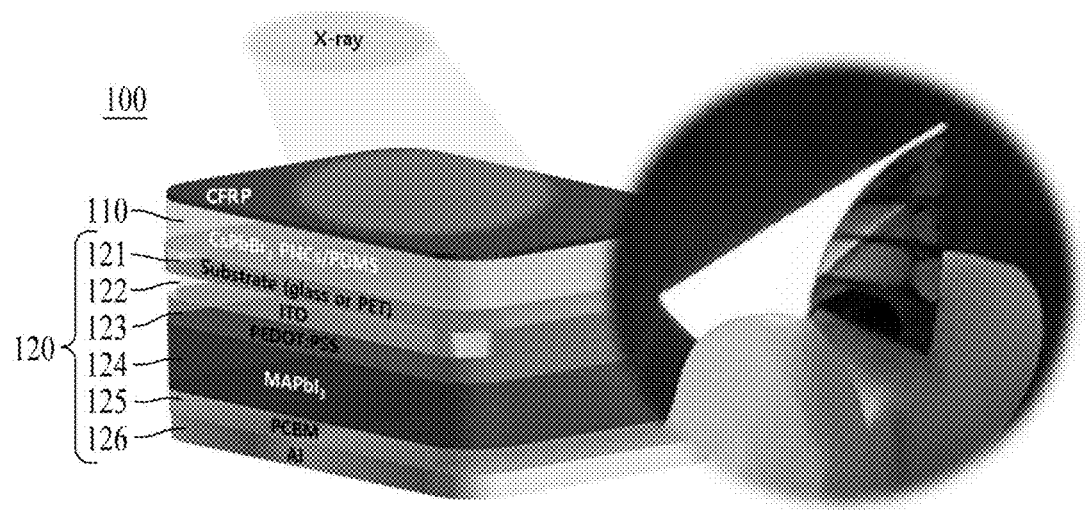
[FIG. 2]
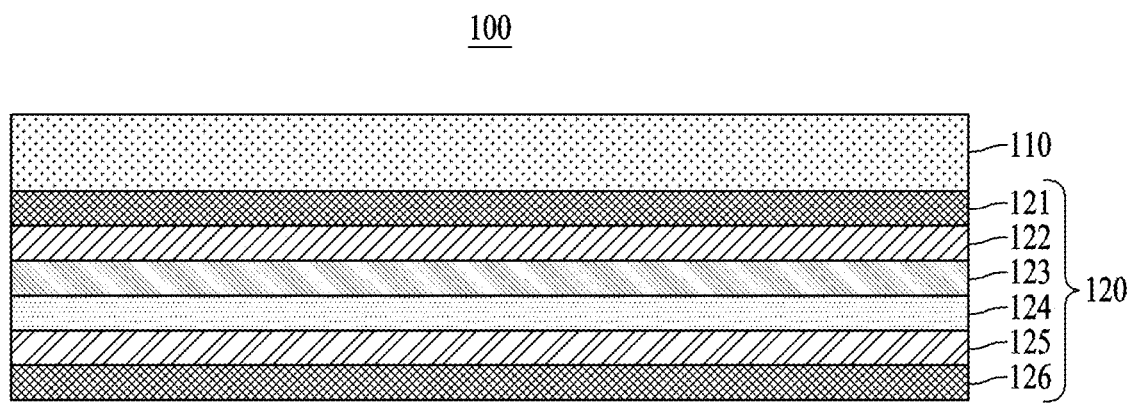

[FIG. 3]
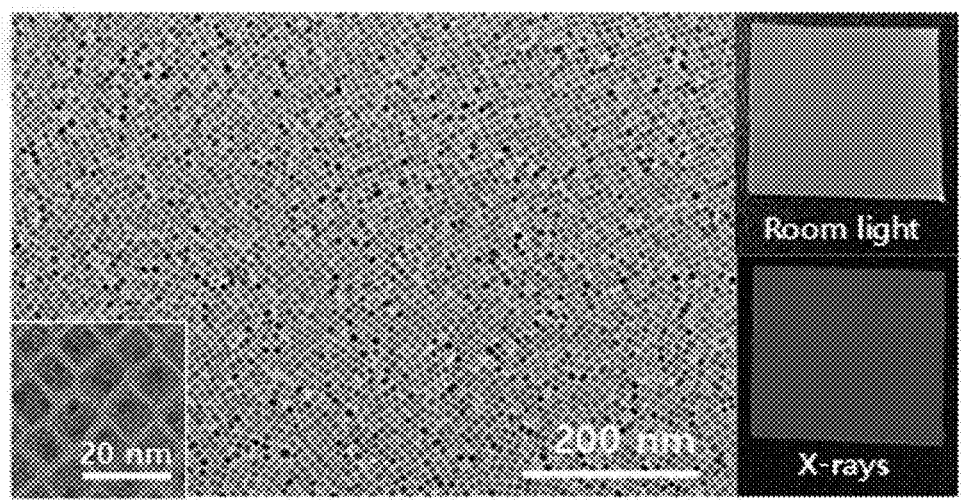
[FIG. 4]
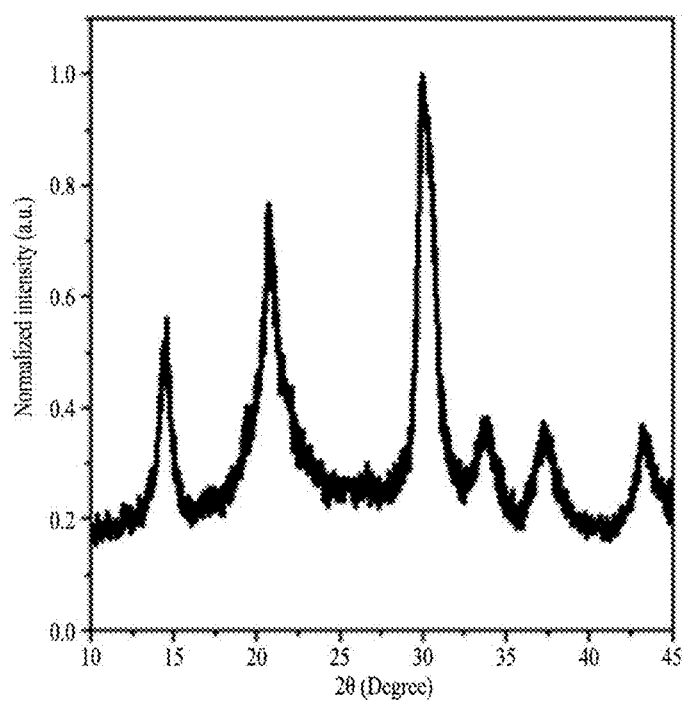

[FIG. 5]
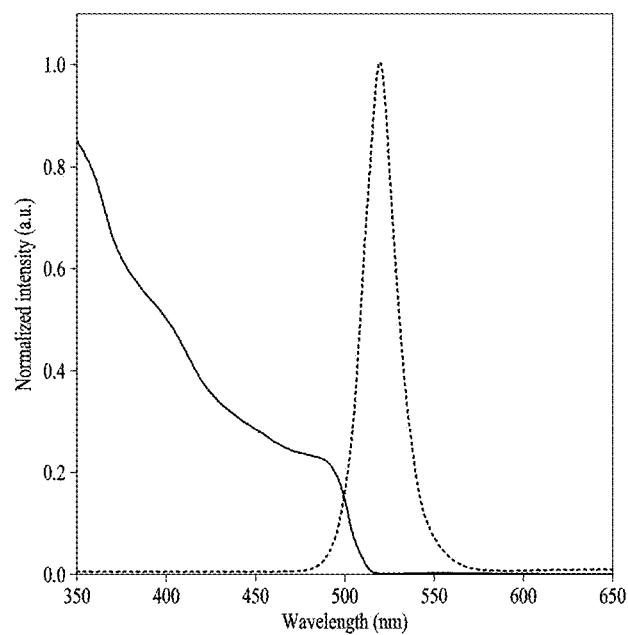
[FIG. 6]
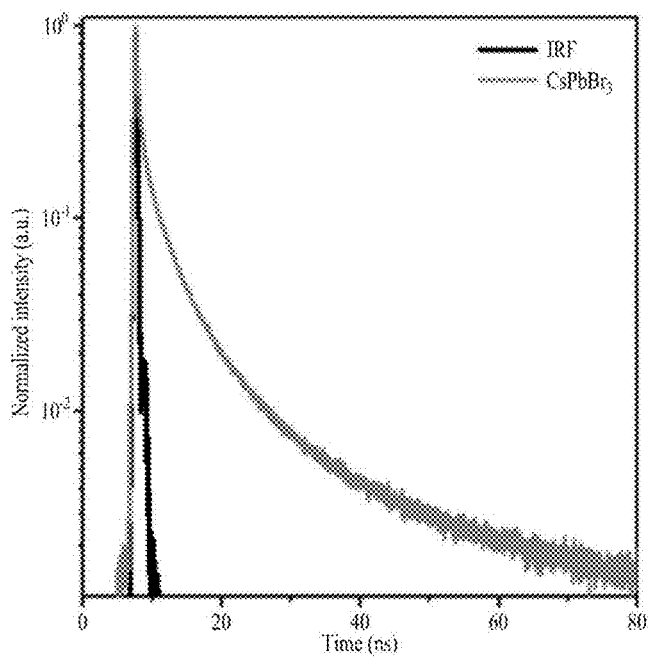

[FIG. 7]
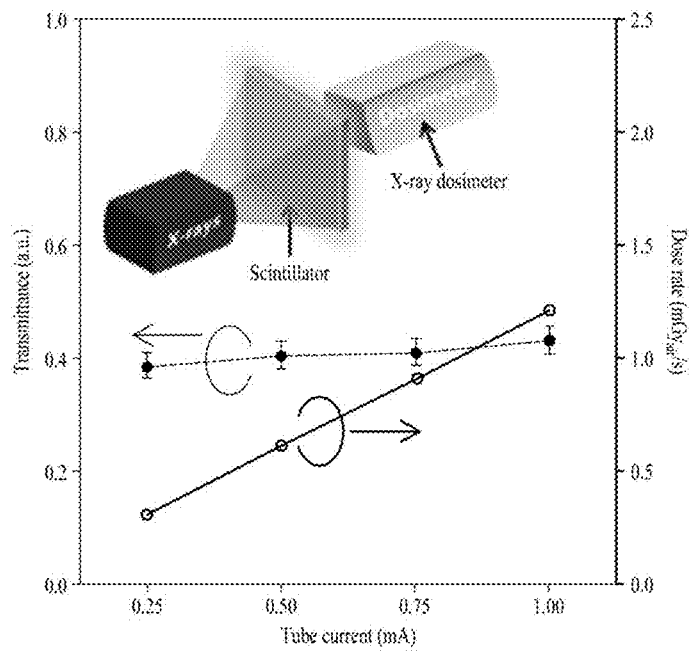
[FIG. 8]
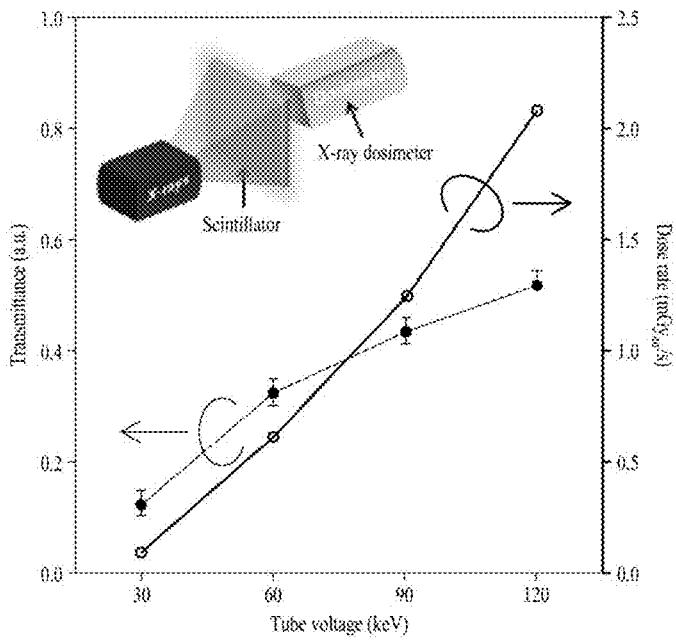

[FIG. 9]
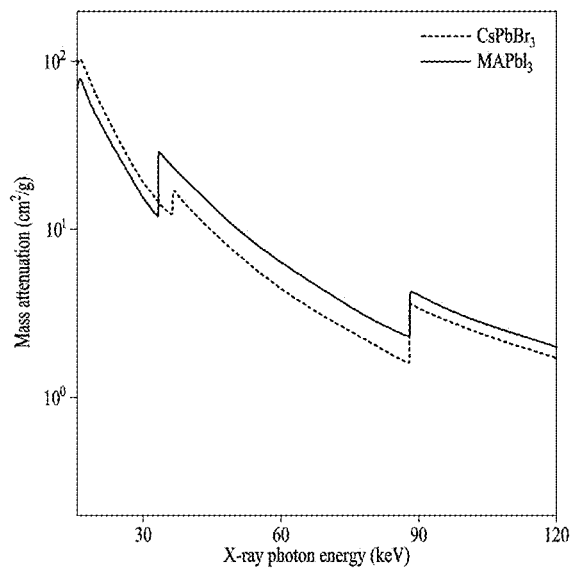
[FIG. 10]
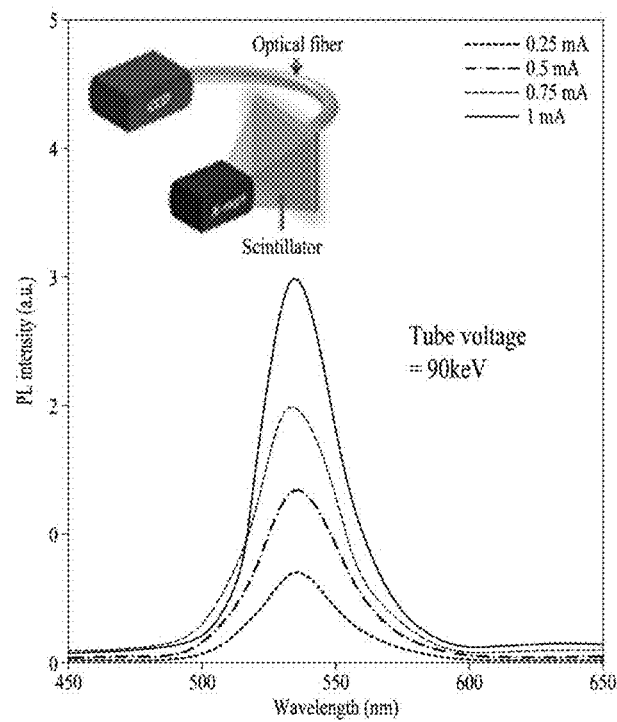

[FIG. 11]
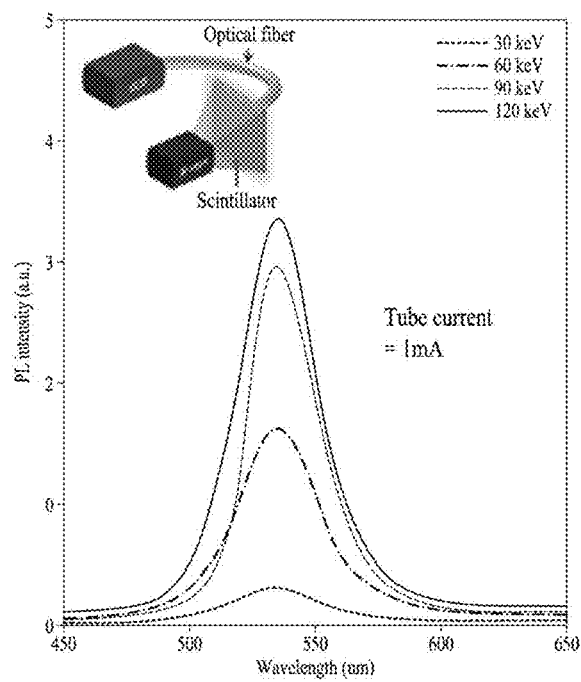
[FIG. 12]
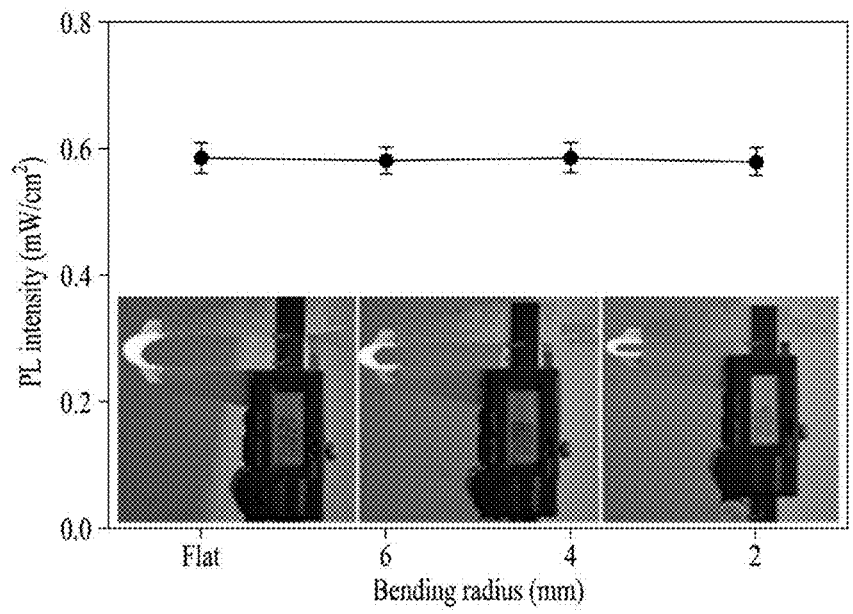

[FIG. 13]
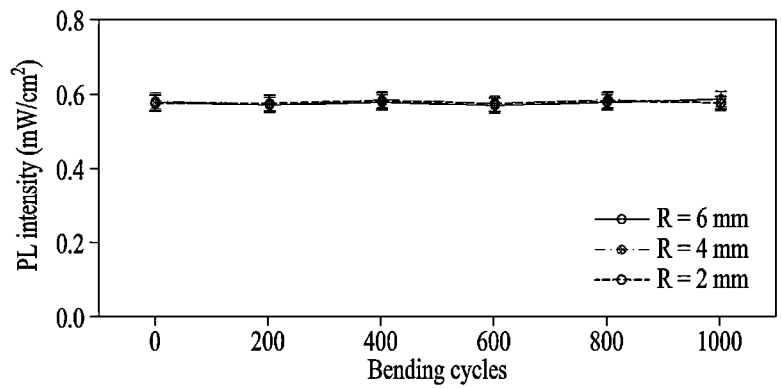
[FIG. 14]
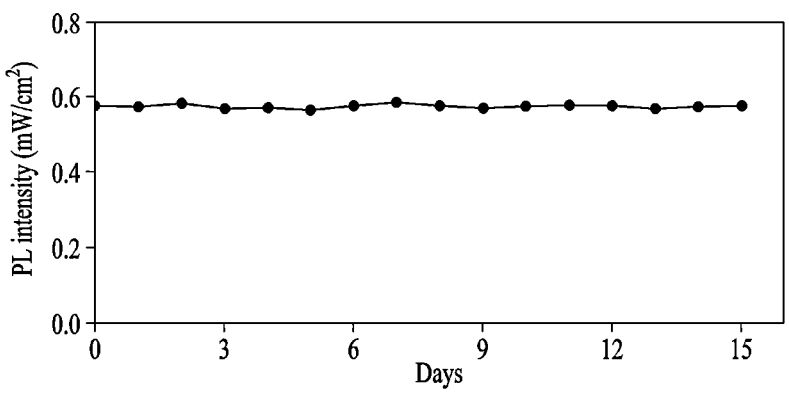
[FIG. 15]
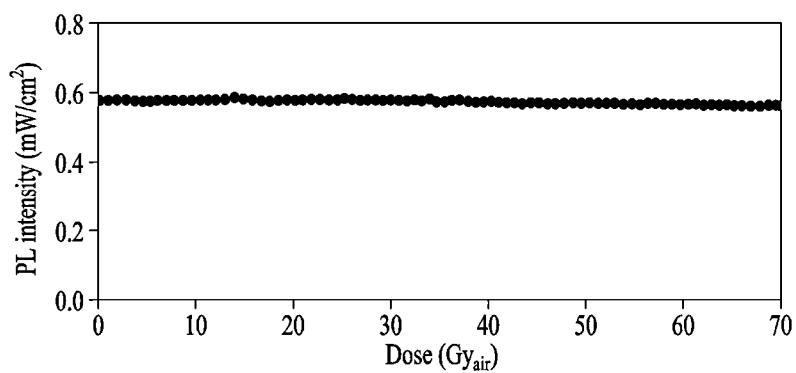

[FIG. 16]
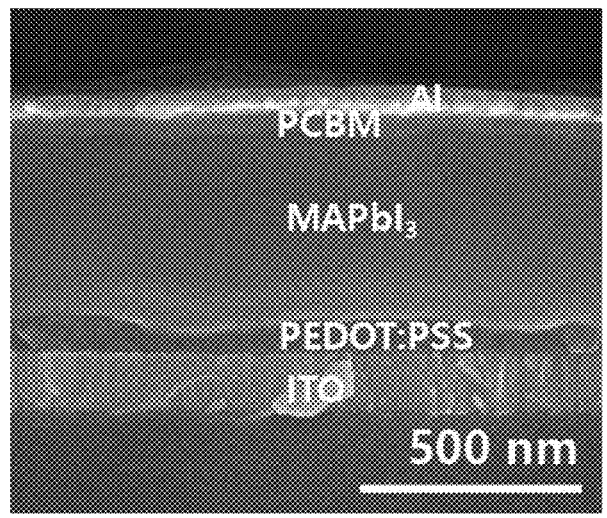
[FIG. 17]
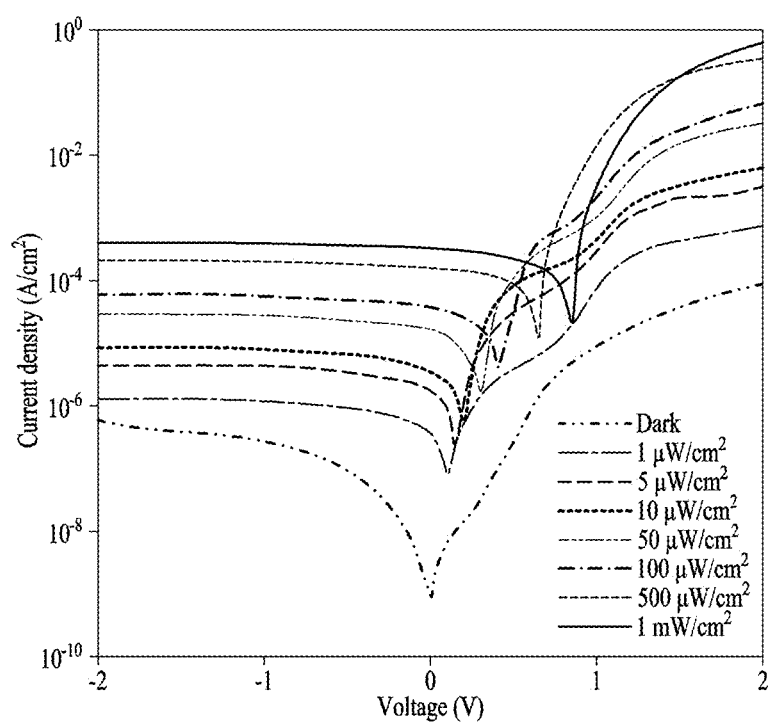

[FIG. 18]
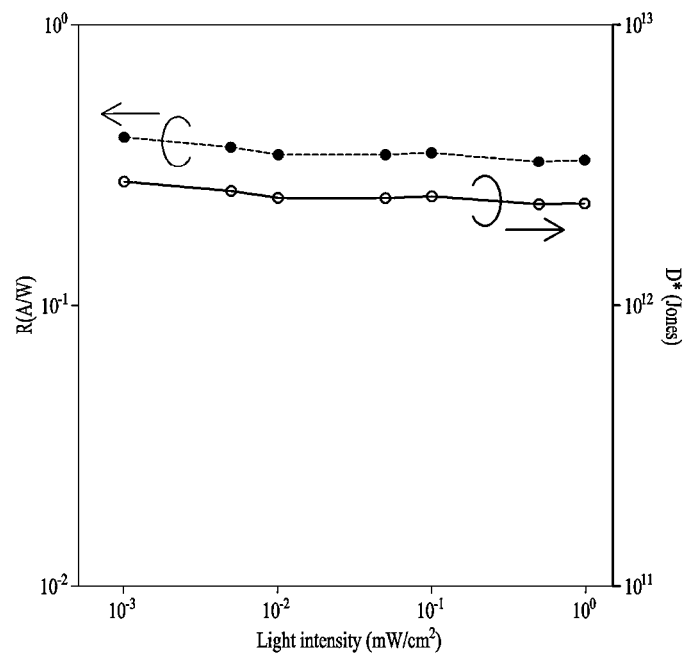
[FIG. 19]
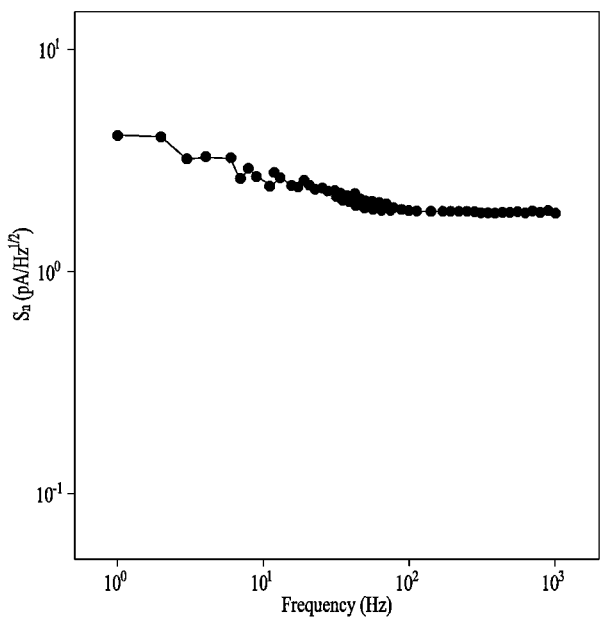

【FIG. 20】
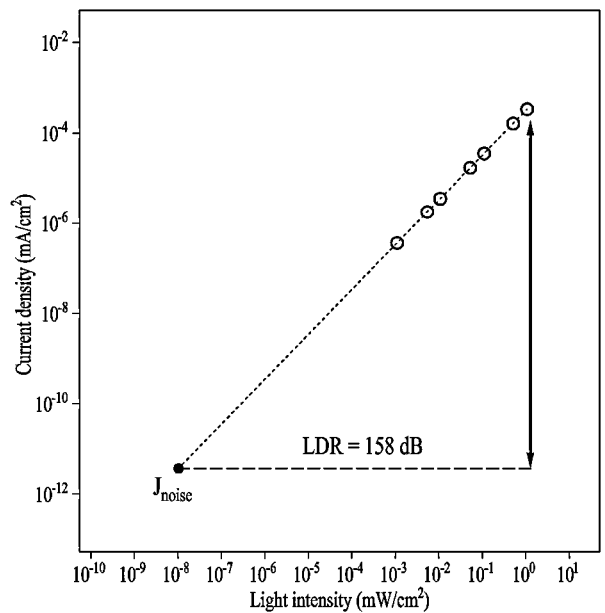
【FIG. 21】
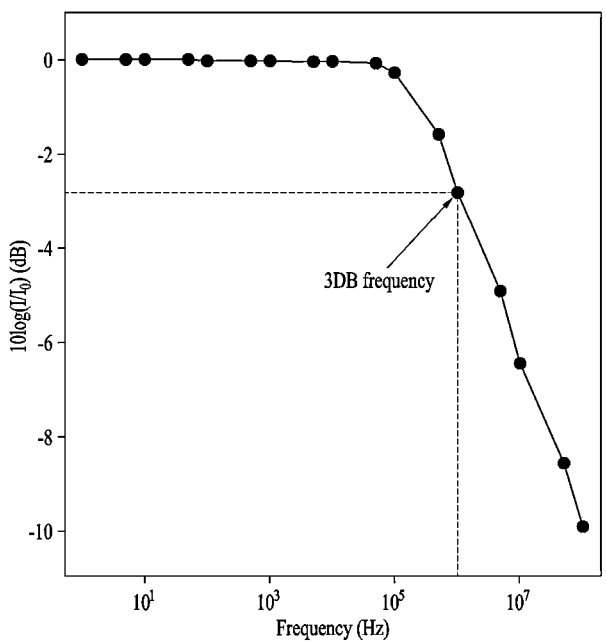

[FIG. 22]
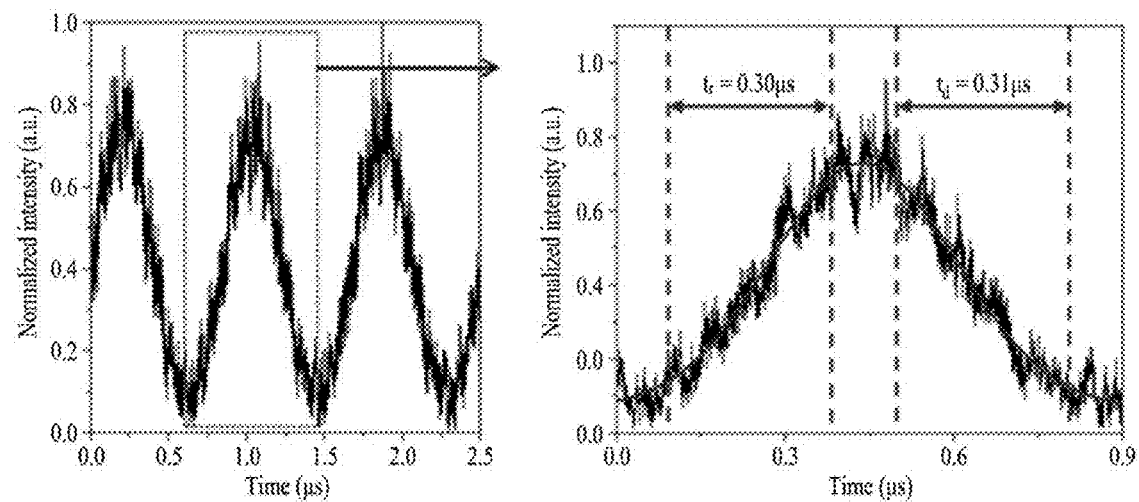
[FIG. 23]
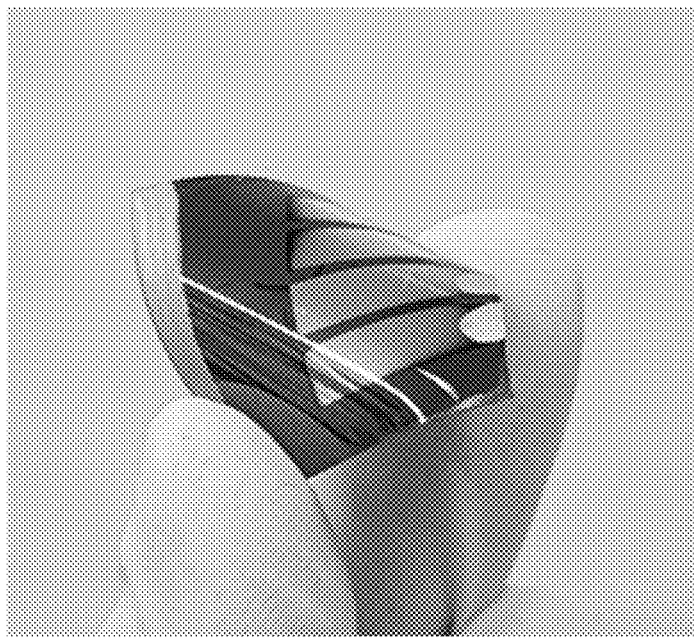

【FIG. 24】
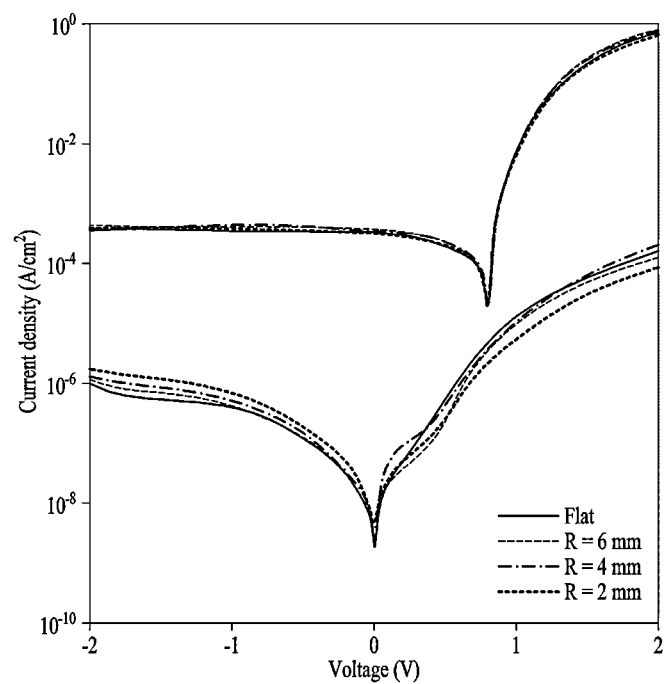
【FIG. 25】
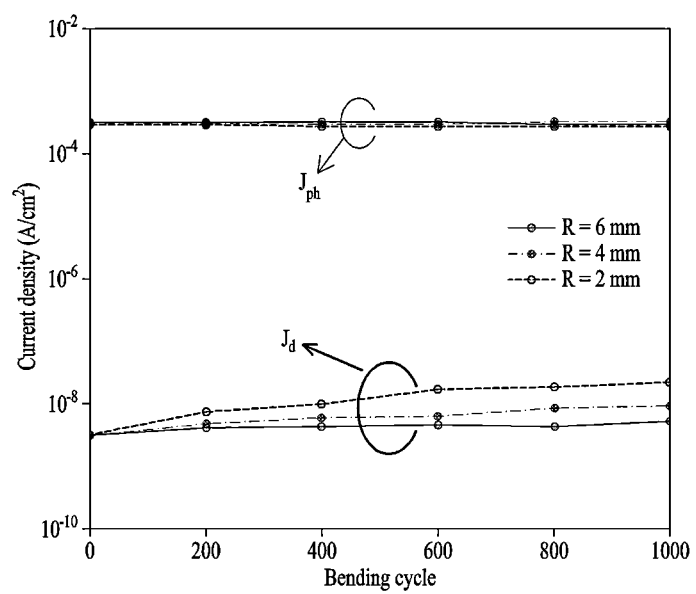

[FIG. 26]
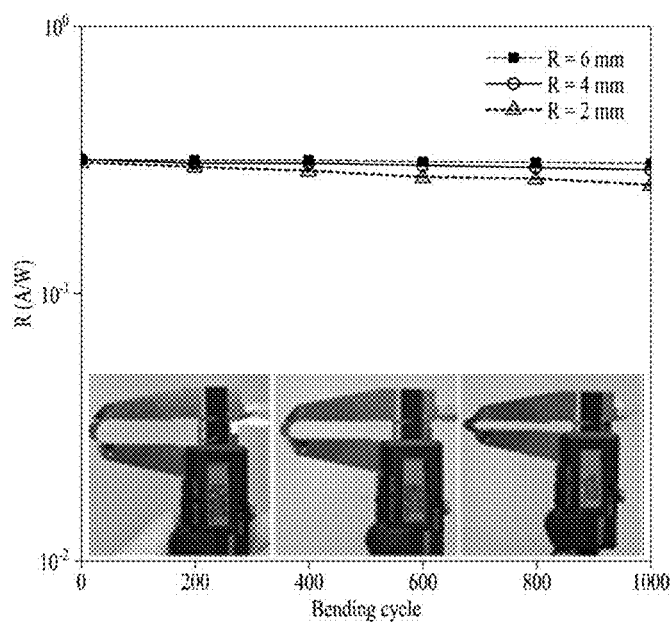
[FIG. 27]
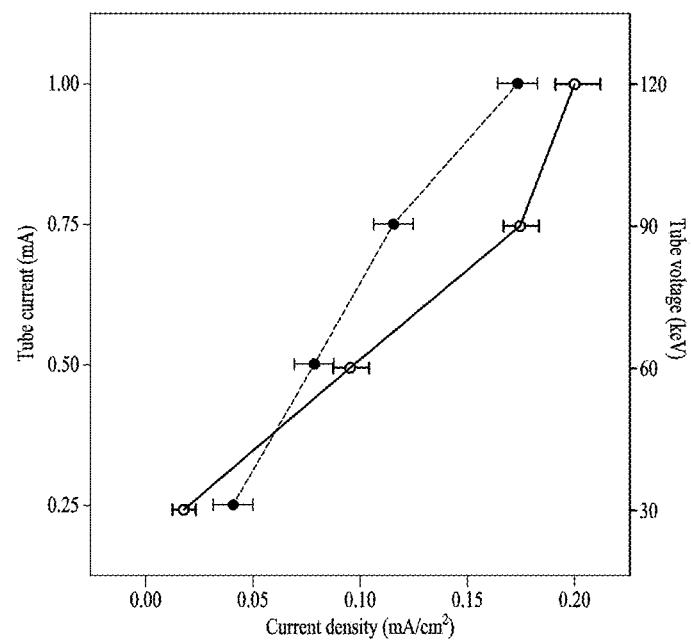

[FIG. 28]
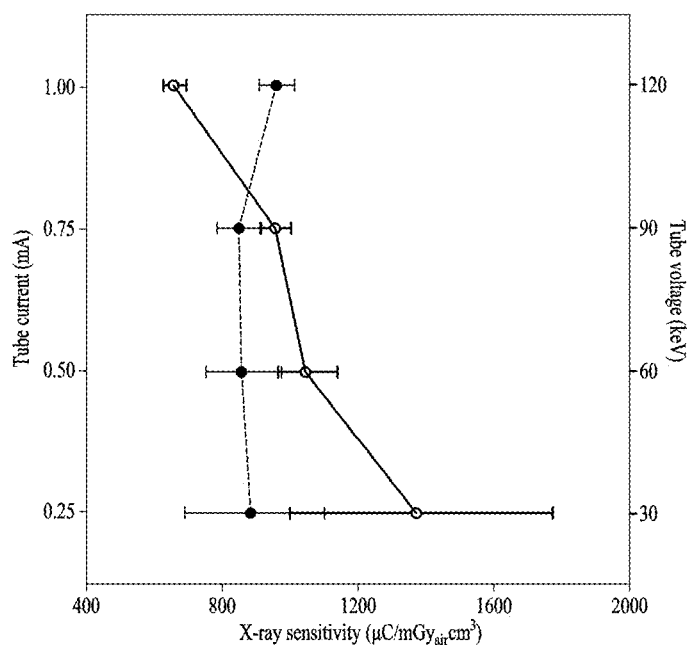
[FIG. 29]
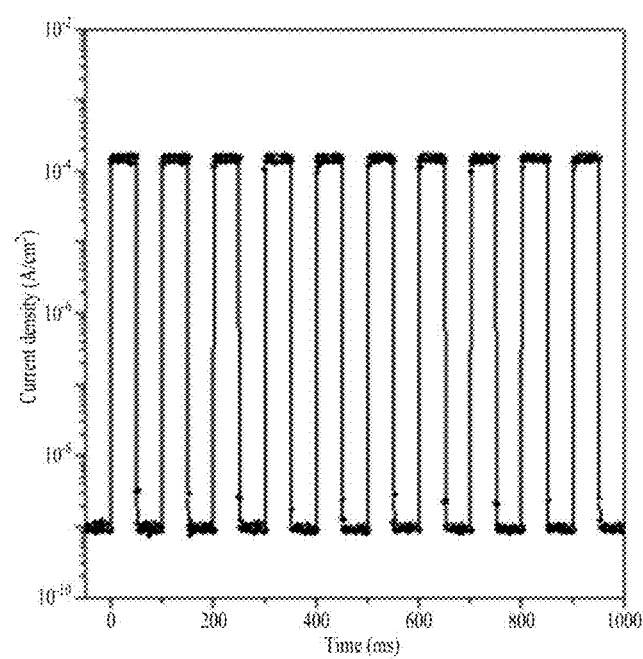

【FIG. 30】
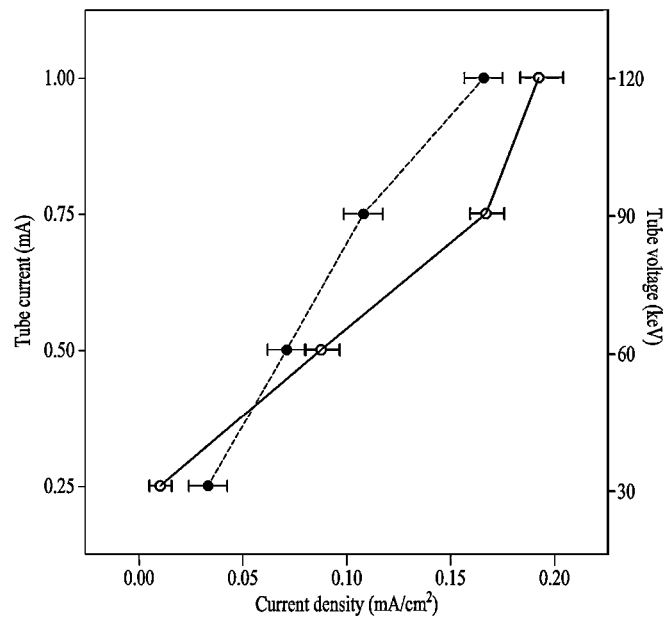
【FIG. 31】
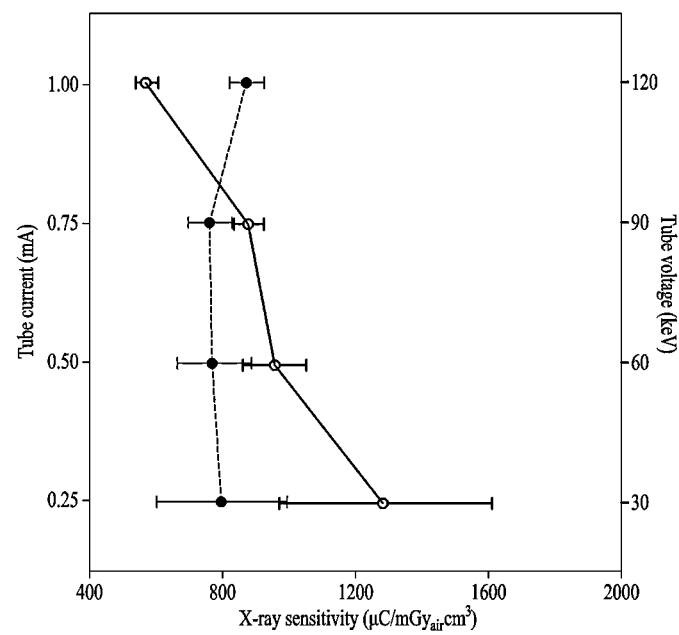

【FIG. 32A】
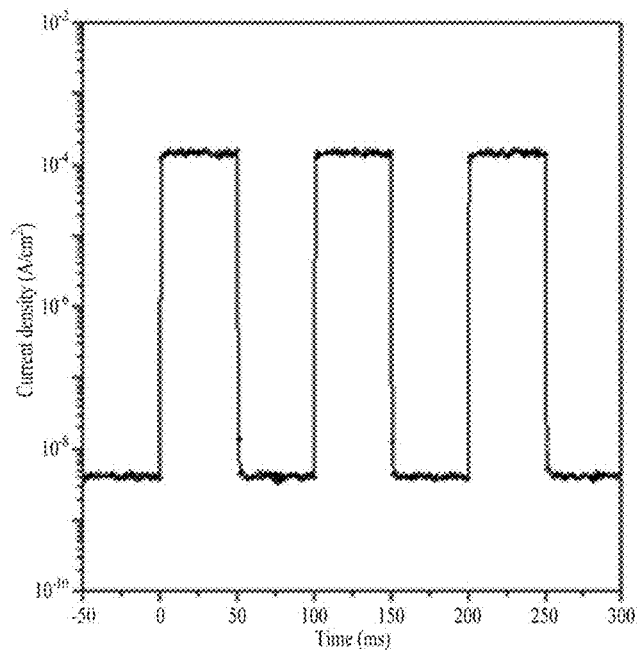
【FIG. 32B】
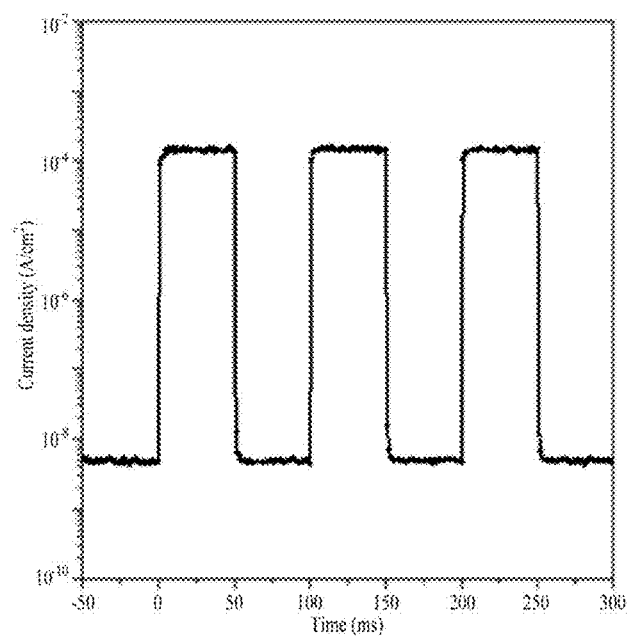

[FIG. 32C]
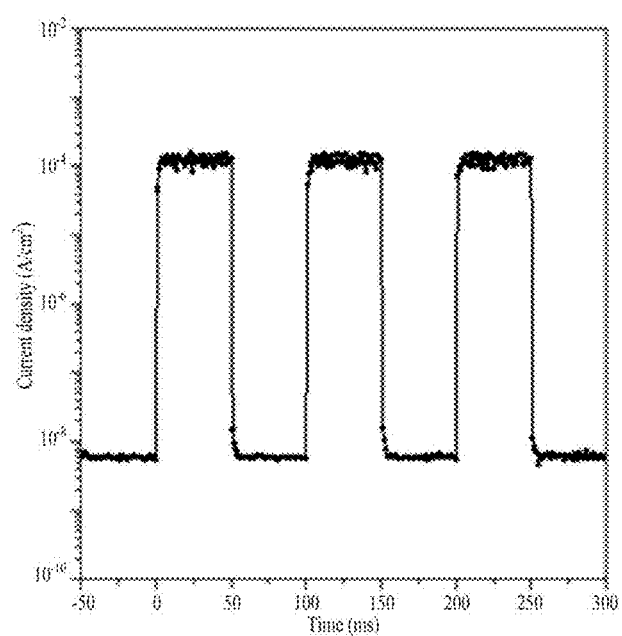

US 11,744,090 B2

SELF-POWERED PEROVSKITE X-RAY DETECTOR

CROSS REFERENCE TO RELATED APPLICATIONS

This application is a U.S. National Stage Application of International Application No. PCT/KR2020/009739, filed on Jul. 23, 2020, which claims the benefit under 35 USC 119(a) and 365(b) of Korean Patent Application No. 10-2019-0088845, filed on Jul. 23, 2019, in the Korean Intellectual Property Office, the entire disclosure of which is incorporated herein by reference for all purposes.

TECHNICAL FIELD

The present invention relates to a self-powered perovskite X-ray detector.

BACKGROUND ART

Since the discovery of X-rays by Wilhelm Röntgen, extensive research has been conducted to find commercial applications in the fields such as crystallography, medical testing and therapy, non-destructive industrial testing, security testing, and space exploration.

Hard x-rays with energies of 5 to 10 keV have been commonly used to obtain X-ray images in the fields, such as crystal structures, mammography, intraoral structures, computed tomography (CT) and airport security scans, due to long penetration depth thereof.

The emission spectrum of an X-ray source can be classified into a spike-shaped characteristic X-ray and a braking radiation X-ray with a broad spectrum.

For example, the characteristic X-ray with an energy of ~30 keV are used for mammography, and the braking radiation X-ray is used for chest radiography.

X-ray detectors can be classified into a direct type and an indirect type.

The direct X-ray detector captures X-ray photoelectrons generated in an X-ray absorption layer such as amorphous Se (a-Se) with a bias voltage directly applied to obtain a high resolution, and can be applied to mammography.

The indirect X-ray detector includes a scintillator such as CsI:Tl and Gd2O2S:Tb, GOS, which absorbs X-rays and emits light, and a photodetector such as an a-Si photodetector.

The indirect X-ray detector occupies most of the market because it is cheaper and more stable than the direct X-ray detect, but it is very difficult to demonstrate an X-ray detector with high sensitivity, high resolution and high scan rate to minimize radiation exposure of patients.

Meanwhile, a flexible X-ray detector is important for analyzing curved structures.

Yakunin et al. reported a direct-type $CH_3NH_3PbI_3$ ($MAPbI_3$) perovskite X-ray detector having high sensitivity (25 $\mu Cm/Gy_{air}$ $cm^3$) and high responsivity ($1.9 \times 10^4$ carrier/photon).

In addition, Wei et al. reported a direct-type $MAPbBr_3$ single-crystal perovskite X-ray detector having a sensitivity of 80 $\mu Cm/Gy_{air}$ $cm^3$ that is four times higher than that of the a-Se detector.

In addition, Kim et al. reported a direct-type perovskite X-ray detector having a large area (50×50 $cm^2$) of 11 $\mu Cm/Gy_{air}$ $cm^3$ which is fabricated by a printing process.

However, since such direct-type perovskite X-ray detectors are fabricated by depositing a very thick crystalline perovskite layer on an array-type thin film transistor (TFT), it is inherently difficult to fabricate a flexible perovskite X-ray detector.

Recently, an indirect-type X-ray detector based on a $CsPbBr_3$ perovskite nanocrystal (PNCs) scintillator has been reported. However, $CsPbBr_3$ PNCs were relatively tightly dispersed in a polymethyl methacrylate (PMMA) matrix for scintillators, and an array-type photodetector was formed on a rigid substrate and thus did not have flexibility.

RELATED ART DOCUMENTS

Patent Documents

Korean Patent No. 10-1839696, "X-RAY DETECTOR HAVING SCINTILLATOR COMPRISING PEROVSKITE COMPOUND"

Korean Patent Application Publication No. 10-2018-0106851, "PHOTOELECTRIC CONVERSION ELEMENT INCLUDING PEROVSKITE COMPOUND AND IMAGING DEVICE INCLUDING THE SAME"

DISCLOSURE

Technical Problem

Therefore, the present invention has been made in view of the above problems, and it is one object of the present invention to provide a self-powered perovskite X-ray detector having a shape wherein a scintillator and a perovskite photodetector are combined. Here, the scintillator and the perovskite photodetector include a perovskite compound. Accordingly, the PL lifespan and reaction characteristics of the scintillator and the perovskite photodetector creates a synergistic effect due to the perovskite compound, so that the PL lifespan and reaction characteristics of the perovskite X-ray detector can be improved.

It is another object of the present invention to provide a self-powered perovskite X-ray detector including a scintillator and perovskite photodetector that are formed of a perovskite compound, and thus, being capable of having high responsivity and specific detectivity.

It is another object of the present invention to provide a self-powered perovskite X-ray detector including a scintillator and perovskite photodetector that are formed of a perovskite compound, and thus, being capable of sensitively detecting X-rays.

It is another object of the present invention to provide a self-powered perovskite X-ray detector including a scintillator and a perovskite photodetector that have flexibility. Accordingly, the perovskite X-ray detector can also have flexibility, and the flexible perovskite X-ray detector can be applied to structures having various bent shapes.

It is another object of the present invention to provide a self-powered perovskite X-ray detector having constant responsivity regardless of a change in a bending radius, and thus, having excellent flexible durability.

It is yet another object of the present invention to provide a self-powered perovskite X-ray detector having almost constant responsivity regardless of the number of repeated bending, and thus, having excellent flexible durability.

Technical Solution

In accordance with an aspect of the present invention, the above and other objects can be accomplished by the provision of a self-powered perovskite X-ray detector, including a perovskite photodetector placed under a scintillator configured to convert incident X-rays into visible light, the perovskite photodetector including: a substrate placed under the scintillator; a first electrode formed under the substrate; a hole transport layer formed under the first electrode; a perovskite light absorption layer formed under the hole transport layer; an electron transport layer formed under the perovskite light absorption layer; and a second electrode formed under the electron transport layer, wherein the scintillator and the perovskite light absorption layer include a perovskite compound represented by Formula 1 below:

$$A_aM_bX_c \quad \text{[Formula 1]}$$

where A is a monovalent cation, M is a divalent metal cation or a trivalent metal cation, X is a monovalent anion, a+2b=c when M is a divalent metal cation, a+3b=4c when M is a trivalent metal cation, and a, b, and c are natural numbers.

In accordance with the perovskite X-ray detector according to the present invention, the flexible perovskite X-ray detector may be a flexible device or a non-flexible device.

In accordance with the perovskite X-ray detector according to the present invention, the scintillator may include at least one of polydimethylsiloxane (PDMS), polyethylene terephthalate (PET), polyethylene naphthalene (PEN), polyimide (PI), triacetyl cellulose (TAC), polyacryl (PA), polyurethane (PU), polyphenylene sulfide (PPS), polyarylate, polycarbonate (PC), and cellulose acetate propionate (CAP).

In accordance with the perovskite X-ray detector according to the present invention, the perovskite compound included in the scintillator may be a nanocrystal.

In accordance with the perovskite X-ray detector according to the present invention, the monovalent cation may be at least one selected from the group consisting of a $C_{1-24}$ linear or branched alkyl group, an amine group (—$NH_3$), a hydroxyl group (—OH), a cyano group (—CN), a halogen group, a nitro group (—NO), a methoxy group (—$OCH_3$) or an imidazolium group-substituted $C_{1-24}$ linear or branched alkyl group, $Li^+$, $Na^+$, $K^+$, $Rb^+$, $Cs^+$, $Fr^+$, $Cu(I)^+$, $Ag(I)^+$ and $Au(I)^+$.

In accordance with the perovskite X-ray detector according to the present invention, the divalent metal cation may include at least one selected from the group consisting of $Pb^{2+}$, $Sn^{2+}$, $Ge^{2+}$, $Cu^{2+}$, $Co^{2+}$, $Ni^{2+}$, $Ti^{2+}$, $Zr^{2+}$, $Hf^{2+}$ and $Rf^{2+}$.

In accordance with the perovskite X-ray detector according to the present invention, the trivalent metal cation may include at least one selected from the group consisting of $In^{3+}$, $Bi^{3+}$, $Co^{3+}$, $Sb^{3+}$, $Ni^{3+}$, $Al^{3+}$, $Ga^{3+}$, $Ti^{3+}$, $Sc^{3+}$, $Y^{3+}$, $La^{3+}$, $Ce^{3+}$, $Fe^{3+}$, $Ru^{3+}$, $Cr^{3+}$, $V^{3+}$ and $Ti^{3+}$.

In accordance with the perovskite X-ray detector according to the present invention, the monovalent anion may include at least one selected from the group consisting of $F^-$, $Cl^-$, $Br^-$, $I^-$, $SCN^-$, $BF_4^-$ and $PF_6^-$.

In accordance with the perovskite X-ray detector according to the present invention, the scintillator may have a transient photoluminescence (transient PL) average lifespan of 0.1 ns to 1000 ns.

In accordance with the perovskite X-ray detector according to the present invention, the scintillator may have a thickness of 1 μm to 1.5 mm.

In accordance with the perovskite X-ray detector according to the present invention, the perovskite light absorption layer may have a thickness of 10 nm to 200 μm.

In accordance with the perovskite X-ray detector according to the present invention, the perovskite photodetector may have a responsivity (R) of 0.0001 A/W to 1 A/W.

In accordance with the perovskite X-ray detector according to the present invention, the perovskite photodetector may have a specific detectivity (D*) of $10^9$ cmHz$^{0.5}$/W to $10^{13}$ cmHz$^{0.5}$/W.

In accordance with the perovskite X-ray detector according to the present invention, the perovskite photodetector may have a reaction time of 0.01 μs to 100 μs.

In accordance with the perovskite X-ray detector according to the present invention, the perovskite X-ray detector may have a current density of 0.00001 mA/cm² to 10 mA/cm².

In accordance with the perovskite X-ray detector according to the present invention, an X-ray sensitivity of the perovskite X-ray detector may be 10 μCmGy$_{air}^{-1}$ cm$^{-2}$ to 1,000 μCmGy$_{air}^{-1}$ cm$^{-2}$ based on an area of an active region.

In accordance with the perovskite X-ray detector according to the present invention, an X-ray sensitivity of the perovskite X-ray detector may be 100 μCmGy$_{air}^{-1}$ cm$^{-3}$ to 1,000 μCmGy$_{air}^{-1}$ cm$^{-3}$ based on a volume of an active region.

Advantageous Effects

According to an embodiment of the present invention, a scintillator including a perovskite compound and a perovskite photodetector including a perovskite compound are combined, so that the PL lifespan and reaction characteristics of the scintillator and the perovskite photodetector can create a synergistic effect due to the perovskite compound, and thus, the PL lifespan and reaction characteristics of the perovskite X-ray detector can be improved.

According to an embodiment of the present invention, both the scintillator and the perovskite photodetector are formed of a perovskite compound, so that the perovskite X-ray detector can have high responsivity and specific detectivity.

According to an embodiment of the present invention, both the scintillator and the perovskite photodetector are formed of a perovskite compound, so that the perovskite X-ray detector can sensitively detect X-rays.

According to an embodiment of the present invention, both the scintillator and the perovskite photodetector have flexibility, so that the perovskite X-ray detector can also have flexibility, and the flexible perovskite X-ray detector can be applied to structures having various bent shapes.

According to an embodiment of the present invention, the perovskite X-ray detector has constant responsivity regardless of a change in a bending radius, thereby being capable of having excellent flexible durability.

According to an embodiment of the present invention, the perovskite X-ray detector has almost constant responsivity regardless of the number of repeated bending, thereby being capable of having excellent flexible durability.

DESCRIPTION OF DRAWINGS

FIG. 1 is a schematic diagram illustrating the overall appearance of a flexible perovskite X-ray detector according to an embodiment of the present invention.

FIG. 2 is a sectional view illustrating a specific shape of a flexible perovskite X-ray detector according to an embodiment of the present invention.

FIG. 3 illustrates an electron transmission microscope (TEM) image of a scintillator according to an embodiment of the present invention and the emission state of the scintillator according to irradiation light.

FIG. 4 illustrates an X-ray diffraction (XRD) pattern of a scintillator according to an embodiment of the present invention.

FIG. 5 illustrates UV-visible and photoluminescence (PL) spectra of a scintillator according to an embodiment of the present invention.

FIG. 6 illustrates a transient PL decay curve of a scintillator according to an embodiment of the present invention.

FIG. 7 illustrates the X-ray dose rate and transmittance according to a tube current of a scintillator according to an embodiment of the present invention.

FIG. 8 illustrates the X-ray dose rate and transmittance according to a tube voltage of a scintillator according to an embodiment of the present invention.

FIG. 9 illustrates X-ray photon energy-dependent mass attenuation of a scintillator according to an embodiment of the present invention and perovskite photodetector.

FIG. 10 illustrates a PL spectrum according to a tube current when a tube voltage of a scintillator according to an embodiment of the present invention is 90 keV.

FIG. 11 illustrates a PL spectrum according to a tube voltage when a tube current of a scintillator according to an embodiment of the present invention is 1 mA.

FIG. 12 illustrates PL intensity according to a bending radius of a scintillator according to an embodiment of the present invention.

FIG. 13 illustrates PL intensity of a scintillator according to an embodiment of the present invention according to the number of repeated bending.

FIG. 14 illustrates PL intensity according to the number of days of use of a scintillator according to an embodiment of the present invention.

FIG. 15 illustrates PL intensity according to X-ray exposure of a scintillator according to an embodiment of the present invention.

FIG. 16 illustrates a scanning electron microscope (SEM) image of a cross-section of a non-flexible perovskite photodetector according to an embodiment of the present invention.

FIG. 17 illustrates a current density-voltage (J-V) curve according to light intensity of a non-flexible perovskite photodetector according to an embodiment of the present invention.

FIG. 18 illustrates responsivity and specific detectivity according to light intensity of a non-flexible perovskite photodetector according to an embodiment of the present invention.

FIG. 19 illustrates a noise spectral density according to a frequency of a non-flexible perovskite photodetector according to an embodiment of the present invention.

FIG. 20 illustrates a linear dynamic range (LDR) of a non-flexible perovskite photodetector according to an embodiment of the present invention.

FIG. 21 illustrates signal attenuation according to a frequency of a non-flexible perovskite photodetector according to an embodiment of the present invention.

FIG. 22 illustrates an output photocurrent signal in a 1 MHz input pulse modulation of a non-flexible perovskite photodetector according to an embodiment of the present invention.

FIG. 23 illustrates a bent state of a flexible perovskite photodetector according to an embodiment of the present invention.

FIG. 24 illustrates a current density-voltage curve according to a bending radius of a flexible perovskite photodetector according to an embodiment of the present invention.

FIG. 25 illustrates a current density of a flexible perovskite photodetector according to an embodiment of the present invention when repeatedly bent.

FIG. 26 illustrates responsivity to repetitive bending of a flexible perovskite photodetector according to an embodiment of the present invention.

FIG. 27 illustrates a current density according to a change in each of the tube current and tube voltage of a non-flexible perovskite X-ray detector according to an embodiment of the present invention.

FIG. 28 illustrates X-ray sensitivity according to a change in each of a tube current and a tube voltage of a non-flexible perovskite X-ray detector according to Example 2 of the present invention.

FIG. 29 illustrates an output signal when an X-ray input signal is applied at 50 ms intervals to a non-flexible perovskite X-ray detector according to Example 2 of the present invention.

FIG. 30 illustrates a current density according to a change in each of a tube current and a tube voltage of a flexible perovskite X-ray detector according to an embodiment of the present invention.

FIG. 31 illustrates X-ray sensitivity according to a change in each of a tube current and a tube voltage of a flexible perovskite X-ray detector according to an embodiment of the present invention.

FIG. 32A illustrates an output signal when a bending radius of a flexible perovskite X-ray detector according to an embodiment of the present invention is 6 mm.

FIG. 32B illustrates an output signal when a bending radius of a flexible perovskite X-ray detector according to an embodiment of the present invention is 4 mm.

FIG. 32C illustrates an output signal when a bending radius of a flexible perovskite X-ray detector according to an embodiment of the present invention is 2 mm.

BEST MODE

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context.

It will be further understood that the terms "comprise" and/or "comprising", when used in this specification, specify the presence of stated steps, but do not preclude the presence or addition of one or more other steps thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the invention and the appended claims, the singular forms "a", "an" and "the" are intended to include the plural forms as well, unless context clearly indicates otherwise.

Although terms used in the specification are selected from terms generally used in related technical fields, other terms may be used according to technical development and/or due to change, practices, priorities of technicians, etc.

Therefore, it should not be understood that terms used below limit the technical spirit of the present invention, and it should be understood that the terms are exemplified to describe embodiments of the present invention.

Also, some of the terms used herein may be arbitrarily chosen by the present applicant. In this case, these terms are defined in detail below. Accordingly, the specific terms used herein should be understood based on the unique meanings thereof and the whole context of the present invention.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

Meanwhile, in the following description of the present invention, a detailed description of known functions and configurations incorporated herein will be omitted when it may make the subject matter of the present invention unclear.

The terms used in the specification are defined in consideration of functions used in the present invention, and can be changed according to the intent or conventionally used methods of clients, operators, and users. Accordingly, definitions of the terms should be understood on the basis of the entire description of the present specification.

FIG. 1 is a schematic diagram illustrating the overall appearance of a flexible perovskite X-ray detector according to an embodiment of the present invention.

Referring to FIG. 1, a perovskite X-ray detector 100 according to an embodiment of the present invention has a shape wherein a scintillator 110 and a perovskite photodetector 120 are combined.

Particularly, the perovskite photodetector 120 may be located under the scintillator 110.

The scintillator 110 according to an embodiment of the present invention converts incident X-rays into visible light and may include a perovskite compound such as $CsPbBr_3$.

In addition, to provide flexibility, the scintillator 110 may include a flexible polymer such as polydimethylsiloxane (PDMS), polyethylene terephthalate (PET), polyethylene naphthalene (PEN), polyimide (PI), triacetyl cellulose (TAC), polyacryl (PA), polyurethane (PU), polyphenylene sulfide (PPS), polyarylate, polycarbonate (PC), cellulose acetate propionate (CAP) or a combination thereof.

The perovskite photodetector 120 according to an embodiment of the present invention may include a substrate 121, a first electrode 122, a hole transport layer 123, a perovskite light absorption layer 124 made of a perovskite compound, an electron transport layer 125, and a second electrode 126.

In addition, to provide flexibility, the perovskite photodetector 120 may be a flexible substrate including a flexible polymer such as polyethylene terephthalate (PET), polyethylene naphthalene (PEN), polyimide (PI), triacetyl cellulose (TAC), polyacryl (PA), polydimethylsiloxane (PDMS), polyurethane (PU), polyphenylene sulfide (PPS), polyarylate, polycarbonate (PC), or cellulose acetate propionate (CAP).

According to an embodiment, the perovskite photodetector 120 may be a non-flexible substrate such as willow glass.

When the perovskite photodetector 120 includes a flexible substrate, the perovskite X-ray detector according to an embodiment of the present invention may be a flexible device.

In addition, when the perovskite photodetector 120 includes a non-flexible substrate, the perovskite X-ray detector according to an embodiment of the present invention may be a non-flexible device.

In the perovskite X-ray detector 100 according to an embodiment of the present invention, the perovskite photodetector 120 may be placed under the scintillator 110 such that the substrate 121 of the perovskite photodetector 120 contacts the scintillator 110.

The perovskite X-ray detector 100 according to an embodiment of the present invention may have flexibility because flexible the scintillator 110 is combined with the flexible perovskite photodetector 120.

According to an embodiment, a carbon fiber reinforced polymer (CFRP) layer may be formed on the scintillator 110 to block external light.

A general photodetector is a photoconductive type and requires an external power source because it receives a current signal value while applying an electric field from the outside.

However, in the case of the perovskite X-ray detector 100 according to an embodiment of the present invention, it is possible to detect X-rays without an external power source because the scintillator 110 is combined with the perovskite photodetector 120.

Particularly, in the case of the perovskite X-ray detector 100 according to an embodiment of the present invention, the perovskite photodetector 120 placed under the scintillator 110 produces electricity when the scintillator 110 emits light by X-rays, and the electricity is inputted as a signal into a circuit. Accordingly, no additional external power source is required.

In addition, both the scintillator 110 and perovskite photodetector 120 included in the perovskite X-ray detector 100 includes a perovskite compound, so that X-ray sensitivity is high and thus X-ray detection efficiency may be improved.

In generally, X-ray detectors may be divided into a direct type (direct conversion type) and an indirect type (indirect conversion type).

A direct-type X-ray detector may include a photoconductor directly generating electric charges (electron-hole pairs) by X-ray irradiation without converting incident X-rays into visible light; and a plurality of pixel electrodes receiving electric charges from the photoconductor and reading the same as electric signals.

On the other hand, an indirect-type X-ray detector includes a scintillator 110 absorbing X-rays to generate visible light; and a photoelectric conversion device for reading visible light generated by the scintillator 110 as an electrical signal.

That is, in the case of the indirect type, the scintillator 110 converts X-rays into visible light, and then the converted visible light is converted into electric charge through a photoelectric conversion device such as a photodiode.

Since the perovskite X-ray detector 100 according to an embodiment of the present invention includes the scintillator 110 and the perovskite photodetector 120, the perovskite X-ray detector 100 may be referred to as an indirect-type X-ray detector.

Hereinafter, the configuration of the perovskite X-ray detector 100 according to an embodiment of the present invention is described in detail with reference to FIG. 2.

FIG. 2 is a sectional view specifically illustrating a flexible perovskite X-ray detector according to an embodiment of the present invention.

Referring to FIG. 2, the perovskite X-ray detector 100 according to an embodiment of the present invention includes a scintillator 110 and a perovskite photodetector 120.

The scintillator 110 converts X-rays incident from the outside into visible light.

When X-rays are irradiated, the scintillator 110 generates excitons, which are neutral pairs formed by combination of excited electrons and holes and move like a single particle, to generate (emit) light. Accordingly, the scintillator 110 may be used without an externally applied voltage. That is, the scintillator 110 serves to emit light.

The scintillator 110 includes a perovskite compound. Particularly, the scintillator 110 may include a perovskite compound having a perovskite structure, as material capable of absorbing X-rays incident from the outside and converting the same into visible light.

The scintillator 110 may include a perovskite compound represent by Formula 1 below:

[Formula 1]

In Formula 1, A is a monovalent cation, M is a divalent metal cation, X is a monovalent anion, a+2b=c, and a, b, and c are natural numbers.

Alternatively, in Formula 1, A is a monovalent cation, M is a trivalent metal cation, X is a monovalent anion, a+3b=4c, and a, b, and c are natural numbers.

According to an embodiment, the perovskite compound included in the scintillator 110 may be a compound form including a perovskite represented by Formula 1 wherein M is a divalent metal cation; and a perovskite represented by Formula 1 wherein M is a trivalent metal cation.

The monovalent cation A may be a monovalent organic cation, a monovalent inorganic cation or a combination thereof.

Particularly, the perovskite compound may be an organic/inorganic hybrid perovskite compound or an inorganic metal halide perovskite compound, depending upon the type of A in Formula 1.

More particularly, when the monovalent cation in Formula 1 a is a monovalent organic cation, the perovskite compound is composed of an organic material A and inorganic materials M and X, and thus, may be an organic/inorganic hybrid perovskite compound composed of an organic material and an inorganic material.

On the other hand, when the monovalent cation in Formula 1 is a monovalent inorganic cation, the perovskite compound is composed of inorganic materials A, M and X, and thus, may be an inorganic metal halide perovskite compound composed of only inorganic materials.

In the case of the organic/inorganic hybrid perovskite compound, it has both the advantages of an organic material and the advantages of an inorganic material. Accordingly, it is easy to fabricate a thick film, reproducibility is high, and durability and stability against X-ray may be improved.

Meanwhile, when the perovskite compound is an inorganic metal halide perovskite compound, it is easy to fabricate a thick film and reproducibility is high, as in the organic/inorganic hybrid perovskite compound.

In addition, in the inorganic metal halide perovskite compound, durability and stability are higher, compared to an organic/inorganic hybrid perovskite, because an organic material is not used.

The monovalent organic cation may be a $C_{1-24}$ linear or branched alkyl group, an amine group ($-NH_3$), a hydroxyl group ($-OH$), a cyano group ($-CN$), a halogen group, a nitro group ($-NO$), a methoxy group ($-OCH_3$) or an imidazolium group-substituted $C_{1-24}$ linear or branched alkyl group or a combination thereof.

The monovalent inorganic cation may be $Li^+$, $Na^+$, $K^+$, $Rb^+$, $Cs^+$, $Fr^+$, $Cu(I)^+$, $Ag(I)^+$, $Au(I)^+$ or a combination thereof.

The divalent metal cation may be $Pb^{2+}$, $Sn^{2+}$, $Ge^{2+}$, $Cu^{2+}$, $Co^{2+}$, $Ni^{2+}$, $Ti^{2+}$, $Zr^{2+}$, $Hf^{2+}$, $Rf^{2+}$ or a combination thereof.

According to an embodiment, When M of Formula 1 is a trivalent metal cation, M may be $In^{3+}$, $Bi^{3+}$, $Co^{3+}$, $Sb^{3+}$, $Ni^{3+}$, $Al^{3+}$, $Ga^{3+}$, $Ti^{3+}$, $Sc^{3+}$, $Y^{3+}$, $La^{3+}$, $Ce^{3+}$, $Fe^{3+}$, $Ru^{3+}$, $Cr^{3+}$, $V^{3+}$, $Ti^{3+}$ or a combination thereof.

The monovalent anion may be $F^-$, $Cl^-$, $Br^-$, $I^-$, $SCN^-$, $BF_4^-$, $PF_6^-$ or a combination thereof.

The perovskite compound represented by Formula 1 may be a combination of an organic material and an inorganic material.

For example, when the monovalent cation is methylammonium (MA), the divalent metal cation is lead (Pb), and the monovalent anion is iodine (I), the perovskite compound may have $MAPbI_3$ a chemical structure.

In addition, when the monovalent cation is cesium (Cs), the divalent metal cation is lead (Pb), and the monovalent anion is bromine (Br), the perovskite compound may have $CsPbBr_3$ as a chemical structure.

According to an embodiment, when the monovalent anion is combined with Br or Cl other than I, the perovskite compound may have $MAPb(I_{1-x}Br_x)_3$ or $MAPb(I_{1-x}Cl_x)_3$, where $0<x<1$, as a chemical structure.

According to an embodiment, the perovskite compound may be in the form of a plurality of nanocrystals (hereinafter referred to as "perovskite nanocrystal") included in the scintillator 110.

The perovskite nanocrystal is used as a light-emitting body in the scintillator 110.

The particle size of the perovskite compound, i.e., the diameter of the perovskite nanocrystal, may be 1 nm to 900 nm, preferably 1 nm to 500 nm.

When the size of the perovskite nanocrystal is less than 1 nm, a band gap is changed due to the particle size, it is difficult to adjust particle size distribution, and fine adjustment is required. Accordingly, it is unfavorable for mass production.

When the size of the perovskite nanocrystal is greater than 900 nm, there is a problem in that efficiency is reduced due to thermal ionization and delocalization of charge carriers at room temperature. In addition, it is difficult to manufacture a product due to a difficult coating process, and application to a flexible X-ray detector is difficult.

To provide flexibility, the scintillator 110 according to an embodiment of the present invention may further include a flexible polymer, such as PDMS, in addition to the perovskite compound.

Particularly, the scintillator 110 may be fabricated by mixing a perovskite nanocrystal, PDMS and a curing agent, and then degassing, and then curing at 60° C. for 12 hours in a nitrogen atmosphere.

A specific method of fabricating the scintillator 110 will be described in the following example and property evaluation section, but the method is not limited thereto.

According to an embodiment, to improve flexibility of the scintillator 110, an organic binder may be further included when the scintillator 110 is fabricated.

The organic binder may be, without being limited to, polyvinyl butyral resin, polyvinyl chloride resin, acrylic resin, phenoxy resin, polyester resin, polyvinyl formal resin, polyamide resin, polystyrene resin, polycarbonate resin, polyvinyl acetate resin, polyurethane resin, an epoxy resin or a combination thereof.

The scintillator 110 may include a perovskite compound and an organic binder in a weight ratio of 90:10 to 10:90.

When the scintillator 110 is excessively included in excess of the weight ratio, angular resolution and resolution in the scintillator 110 are decreased. Accordingly, the performance of an X-ray detector may be decreased.

According to an embodiment, an inorganic binder may be further included upon fabrication of the scintillator 110 such that the scintillator 110 has good adhesion to the substrate 121 of the perovskite photodetector 120.

Particularly, the inorganic binder may be included, together with the perovskite compound, in the scintillator 110, thereby improving adhesion of the scintillator 110.

More particularly, when the scintillator 110 includes an inorganic binder together with the perovskite compound, adhesive strength between the perovskite compound and the inorganic binder is improved, thereby improving adhesion to a deposition substrate.

The inorganic binder may include at least one selected from the group consisting of $TiO_2$ nanoparticles, $SiO_2$ nanoparticles, $Al_2O_3$ nanoparticles, $VO_2$ nanoparticles, a layered compound, a metal alkoxide, a metal halide, and the like.

The scintillator 110 may include a perovskite compound and an inorganic binder in a weight ratio of 90:10 to 10:90.

When the scintillator 110 excessively includes the inorganic binder in excess of the weight ratio, angular resolution and resolution are decreased. Accordingly, the performance of an X-ray detector may be decreased.

The inorganic binder may have a particle size of 1 nm to 100 nm. When the particle size of the inorganic binder is less than 1 nm, there is a problem in uniformly controlling particles. When the particle size of the inorganic binder is greater than 100 nm, X-ray scattering increases, so that it is difficult to realize a high-resolution image.

The scintillator 110 may be fabricated by forming a scintillator on a glass substrate by a solution coating method or deposition method using a perovskite compound solution in which a perovskite compound is dissolved in a solvent, and then separating the scintillator from the glass substrate.

The solution coating method may be, for example, spin coating, spray coating, ultra-spray coating, electrospinning coating, slot die coating, gravure coating, bar coating, roll coating, dip coating, shear coating, screen printing, inkjet printing, nozzle printing, or the like.

The deposition method may be, for example, sputtering, atomic layer deposition (ALD), chemical vapor deposition (CVD), thermal evaporation, co-evaporation, plasma enhanced chemical vapor deposition (PECVD), or the like under a reduced pressure condition, an atmospheric pressure condition or a pressurized condition.

Preferably, the scintillator 110 may be formed by a solution process, thereby simplifying a fabrication process and thus reducing manufacturing costs.

The scintillator 110 is preferably made in the form of a thick film so as to absorb X-ray having high energy.

According to an embodiment, the thickness of the scintillator 110 may be controlled depending upon the application field of the perovskite X-ray detector 100 according to an embodiment of the present invention.

Particularly, the scintillator 110 may be fabricated to a thickness of 1 μm to 1.5 mm. The thickness of the scintillator 110 exceeds 1.5 mm, light scattered from the scintillator 110 increases, so that required spatial resolution cannot be satisfied.

In addition, when the thickness of the scintillator 110 is less than 1 μm, there is a disadvantage in that a signal is weakened to a noise level due to a small amount of X-ray absorption.

According to an embodiment, the scintillator 110 may be formed in the form of a film.

Particularly, the scintillator 110 may be formed in the form of a film (thin film) wherein perovskite nanocrystals having a nanocrystal structure are stacked layer by layer.

Alternatively, when the size of the perovskite nanocrystal is large, a space between the perovskite nanocrystals may be filled with a binder material, whereas when the size of the perovskite nanocrystal is small, a space between the perovskite nanocrystals may not be filled with a binder due to a high filling rate.

The scintillator 110 according to an embodiment of the present invention may have excellent photoluminescence (PL) lifespan.

In addition, since the scintillator 110 according to an embodiment of the present invention includes a nanocrystal-shaped perovskite compound, exciton binding energy is increased so that transient PL average lifespan is short.

Particularly, the transient PL average lifespan of the scintillator 110 may be 0.1 ns to 1000 ns.

When the transient PL average lifespan of the scintillator 110 is less than 0.1 ns, traps in the scintillator 110 excessively increase so that light is emitted shorter than a detectable time, which makes it difficult to detect. When the transient PL average lifespan of the scintillator 110 is greater than 1000 ns, images overlap and a response speed is lowered due to a long duration of light emission when a high-speed image such as a moving picture is desired to be obtained.

The perovskite photodetector 120 according to an embodiment of the present invention is placed under the scintillator 110 and converts visible light, converted by the scintillator 110, into an electrical signal.

According to an embodiment, the perovskite photodetector 120 may include a photodiode (PD, not shown).

The photodiode (PD) may convert visible light into an electrical signal.

Particularly, the perovskite photodetector 120 may include a photodiode (PD) formed in each of a plurality of pixel regions on the substrate 121. The photodiode (PD) may absorb visible light converted from X-ray by the scintillator 110 to convert the visible light into an electrical signal.

The perovskite photodetector 120 according to an embodiment of the present invention may generate an electrical signal corresponding to the intensity of incident visible light.

According to an embodiment, the perovskite photodetector 120 may provide the generated electrical signal to a thin film transistor (TFT) (not shown) and capacitor (not shown) placed in the substrate 121.

That is, visible light incident on the perovskite photodetector 120 is converted into charges composed of electrons and holes in the perovskite photodetector 120, and the electrons and holes move along the direction of electric field formed by a capacitor (not shown), and current flows inside the perovskite photodetector 120.

The perovskite photodetector 120 may include a silicon photodiode as a photodiode (PD).

According to an embodiment, the silicon photodiode may be formed of amorphous silicon or (micro)crystalline silicon.

When the silicon photodiode is formed of crystalline silicon, an afterimage included in an image obtained by an X-ray detector may be reduced, compared to the case wherein a photoelectric conversion region is formed of amorphous silicon.

According to an embodiment, the silicon photodiode may be a positive negative (PN)-type photodiode composed of a positive (P)-type semiconductor layer and a negative (N)-type semiconductor layer; a positive intrinsic negative (PIN)-type photodiode composed of a P-type semiconductor layer, an intrinsic (I)-type semiconductor layer and an N-type semiconductor layer; a Schottky-type photodiode; or an avalanche-typephotodiode, preferably a PIN-type photodiode.

According to an embodiment, the P-type, I-type and N-type semiconductor layers may be formed of amorphous or microcrystalline silicon, the P-type semiconductor layer may be formed of, for example, a silicon material doped with a p-type impurity such as boron (B) or potassium (K), the I-type semiconductor layer may be formed of, for example, a silicon material not containing impurities, and the N-type semiconductor layer may be formed of, for example, a silicon material doped with an n-type impurity such as phosphorus (P), arsenic (As), or antimony (Sb).

When the PIN-type photodiode is used as the silicon photodiode, visible light passes through the P-type amorphous silicon layer and is absorbed by the I-type amorphous silicon layer, and, when electrons and holes are generated by visible light having greater energy than an optical band gap of the amorphous silicon within the I-type amorphous silicon layer, electrons and holes generated in the I-type amorphous silicon layer may be collected into the P-type amorphous silicon layer and the N-type amorphous silicon layer by an internal electric field. In addition, electrons and holes may be supplied to an external circuit through an electrode.

According to an embodiment, the silicon photodiode may be formed by ion implant, epitaxial growth, deposition or a solution process.

The perovskite photodetector 120 according to an embodiment of the present invention includes the substrate 121 placed under the scintillator 110, the first electrode 122 formed under the substrate 121, the hole transport layer 123 formed under the first electrode 122, the perovskite light absorption layer 124 formed under the hole transport layer 123, the electron transport layer 125 formed under the perovskite light absorption layer 124 and the second electrode 126 formed under the electron transport layer 125.

The perovskite photodetector 120 is fabricated by forming the first electrode 122 on the substrate 121, forming the hole transport layer 123 on the first electrode 122, forming the perovskite light absorption layer 124 on the hole transport layer 123, forming the electron transport layer 125 on the perovskite light absorption layer 124, and forming the second electrode 126 on the electron transport layer 125. Next, the perovskite photodetector 120 is generally placed upside down such that a lower part of the scintillator 110 comes into contact with the substrate 121, thereby bring the scintillator 110 into contact with the perovskite photodetector 120.

However, in the description of the present invention, it is assumed that the constructions of the perovskite photodetector 120 are sequentially stacked in a direction from an upper surface to a lower surface of the scintillator 110 with respect to the scintillator 110 for convenience of explanation.

The substrate 121 may be an inorganic material substrate or an organic material substrate. To impart flexibility to the perovskite photodetector 120, an organic material substrate is preferred.

The inorganic material substrate may be formed of, without being limited to, glass, quartz, $Al_2O_3$, SiC, Si, GaAs or InP.

The organic material substrate may be selected from, without being limited to, Kepton foil, polyimide (PI), polyethersulfone (PES), polyacrylate (PAR), polyetherimide (PEI), polyethylene naphthalate (PEN), polyethylene terephthalate (PET), polyphenylene sulfide (PPS), polyarylate, polycarbonate (PC), cellulose triacetate (CTA) and cellulose acetate propionate (CAP).

According to an embodiment, the substrate 121 is more preferably formed of a transparent material through which light is transmitted and, in general, the substrate 121 may be any one that can be placed on a front electrode.

According to an embodiment, the substrate 121 may be an array substrate including a complementary metal-oxide semiconductor (CMOS), a charge coupled device (CCD,) or a thin film transistor (TFT).

According to an embodiment, the array substrate may include a thin film transistor (TFT) (not shown) and a capacitor (not shown).

The thin film transistor (TFT) (not shown) may serve as a switching element for sequentially outputting electrical signals generated by the perovskite photodetector 120 to an external circuit.

In addition, the capacitor (not shown) may be located on the substrate 121 so as to accumulate electrical signals converted by the perovskite photodetector 120 or may be installed under each thin film transistor (TFT). However, the perovskite photodetector 120 may also serve as a capacitor (not shown) depending upon the capacity of the perovskite photodetector 120.

According to an embodiment, the substrate 121 may be formed of an insulating material.

The substrate 121 may be made of, for example, glass, quartz, silicon or plastic, but so as to impart flexibility to the perovskite photodetector 120 according to an embodiment of the present invention, the substrate 121 is preferably formed of silicon or plastic.

For example, the plastic substrate may be used for a flexible or bendable X-ray detector, and, when the silicon substrate is processed to a thickness of 100 μm or less, the silicon substrate may be used for a bendable X-ray detector.

The first electrode 122 is formed under the substrate 121 and in particular, a transparent conductive electrode is preferred to improve light transmission.

For example, the first electrode 122 may correspond to a front electrode which is an electrode provided on a light-receiving side.

The first electrode 122 may be formed on the substrate 121 by thermal evaporation, e-beam evaporation, radio frequency sputtering (RF sputtering), magnetron sputtering, vacuum deposition, chemical vapor deposition, or the like.

According to an embodiment, the first electrode 122 may include a transparent conductive electrode having an OMO (O=organic (organic material) or metal oxide, M=metal) structure.

According to an embodiment, the first electrode 122 may be formed on an interlayer insulating layer (not shown)

formed to conformally cover the substrate 121 on which a thin film transistor (not shown) and a capacitor (not shown) are formed.

According to an embodiment, the first electrode 122 may be a plurality of pixel electrodes. Particularly, the first electrode 122 may be formed in a unit of a plurality of pixels on the substrate 121 to form a pixel array constituting an X-ray image.

According to an embodiment, the first electrode 122 may be made of a conductive material having excellent electrical characteristics.

For example, the first electrode 122 may be formed to include, without being limited to, at least one selected from the group consisting of aluminum (Al), silver (Ag), gold (Au), copper (Cu), palladium (Pd), platinum (Pt), indium tin oxide (ITO), indium zinc oxide (IZO), aluminum zinc oxide (AZO), fluorine tin oxide (FTO), carbon nano tube (CNT), graphene and polyethylenedioxythiophene:polystyrenesulfonate (PEDOT:PSS).

The hole transport layer 123 may be formed under the first electrode 122 and, particularly, may be formed between the first electrode 122 and the perovskite light absorption layer 124.

The hole transport layer 123 may allow holes generated in the perovskite light absorption layer 124 to smoothly move to the first electrode 122 and/or the second electrode 126 and may reduce dark current.

According to an embodiment, the hole transport layer 123 may be formed between the perovskite light absorption layer 124 and the second electrode 126 or may be on both upper and lower surfaces of the perovskite light absorption layer 124.

For example, the hole transport layer 123 may include, without being limited to, at least one of a thiophene-based material, a paraphenylenevinylene-based material, a carbazole-based material, and a triphenylamine-based material.

Alternatively, the hole transport layer 123 may be formed of, without being limited to, at least one of P3HT (poly[3-hexylthiophene]), MDMO-PPV (poly[2-methoxy-5-(3',7'-dimethyloctyloxy)]-1,4-phenylene vinylene), MEH-PPV (poly[2-methoxy-5-(2''-ethylhexyloxy)-p-phenylene vinylene]), P3OT (poly (3-octyl thiophene)), POT (poly (octyl thiophene)), P3DT (poly (3-decyl thiophene)), P3DDT (poly (3-dodecyl thiophene), PPV (poly (p-phenylene vinylene)), TFB (poly (9,9'-dioctylfluorene-co-N-(4-butylphenyl)diphenyl amine), Polyaniline, Spiro-MeOTAD ([2,22',7,77'-tetrkis (N,N-dipmethoxyphenylamine)-9,9,9'-spirobi fluorine]), CuSCN, CuI, $MoO_x$, $VO_x$, $NiO_x$, $CuO_x$, PCPDTBT (Poly[2,1,3-benzothiadiazole-4,7-diyl[4,4-bis(2-ethylhexyl-4H-cyclopenta [2,1-b:3,4-b]dithiophene-2,6-diyl]], Si-PCPDTBT (poly[(4,4'-bis(2-ethylhexyl)dithieno[3,2-b:2',3'-d]silole)-2,6-diyl-alt-(2,1,3-benzothiadiazole)-4,7-diyl]), PBDTTPD (poly ((4,8-diethylhexyloxyl) benzo ([1,2-b:4,5-b']dithiophene)-2,6-diyl)-alt-((5-octylthieno[3,4-c]pyrrole-4,6-dione)-1,3-diyl)), PFDTBT (poly[2,7-(9-(2-ethylhexyl)-9-hexyl-fluorene)-alt-5,5-(4',7,-di-2-thienyl-2',1',3'-benzothiadiazole)]), PFO-DBT (poly[2,7-.9,9-(dioctyl-fluorene)-alt-5,5-(4',7'-di-2-.thienyl-2',1',3'-benzothiadiazole)]), PSiFDTBT (poly[(2,7-dioctylsilafluorene)-2,7-diyl-alt-(4,7-bis(2-thienyl)-2,1,3-benzothiadiazole)-5,5'-diyl]), PSBTBT (poly[(4,4'-bis(2-ethylhexyl)dithieno[3,2-b:2',3'-d]silole)-2,6-diyl-alt-(2,1,3-benzothiadiazole)-4,7-diyl]), PCDTBT (Poly [[9-(1-octylnonyl)-9H-carbazole-2,7-diyl]-2,5-thiophenediyl-2,1, 3-benzothiadiazole-4,7-diyl-2,5-thiophenediyl]), PFB (poly (9,9'-dioctylfluorene-co-bis(N,N'-(4,butylphenyl))bis(N,N'-phenyl-1,4-phenylene)diamine), F8BT (poly (9,9'-dioc-tylfluorene-cobenzothiadiazole), PEDOT (poly (3,4-ethyl-enedioxythiophene)), PEDOT:PSS, poly (3,4-ethylenedioxythiophene) poly (styrenesulfonate), PTAA (poly (triarylamine)), poly (4-butylphenyldiphenyl-amine), 4,4'-bis[N-(1-naphtyl)-N-phenylamino]-biphenyl (NPD), PEDOT:PSSbis(N-(1-naphthyl-n-phenyl))benzidine (α-NPD) mixed with PFI (perfluorinated ionomer), N,N'-di (naphthalen-1-yl)-N,N'-diphenyl-benzidine (NPB), N,N'-di-phenyl-N,N'-bis(3-methylphenyl)-1,1'-diphenyl-4,4'-di-amine (TPD), copper phthalocyanine (CuPc), 4,4',4''-tris(3-methylphenylamino)triphenylamine (m-MTDATA), 4,4',4''-tris (3-methylphenylamino)phenoxybenzene (m-MTDAPB), 4,4',4''-tri (N-carbazolyl)triphenylamine (TCTA) and 4,4',4'''-tris (N-(2-naphthyl)-N-phenylamino)-triphenylamine (2-TNATA) as starburst-type amines, and a copolymer thereof.

The hole transport layer 123 may be formed by various solution coating methods using solutions, or various deposition methods.

The solution coating method may be, for example, spin coating, spray coating, ultra-spray coating, electrospinning coating, slot die coating, gravure coating, bar coating, roll coating, dip coating, shear coating, screen printing, inkjet printing, nozzle printing, or the like.

The deposition method may be, for example, sputtering, atomic layer deposition, chemical vapor deposition, thermal evaporation, co-evaporation, plasma enhanced chemical vapor deposition, or the like under a reduced pressure condition, an atmospheric pressure condition or a pressurized condition.

The hole transport layer 123 serves to move holes to the perovskite light absorption layer 124, allows holes to be effectively transferred to the perovskite light absorption layer 124, and may improve efficiency by balancing the densities of holes and electrons in the perovskite light absorption layer 124.

The perovskite light absorption layer 124 is formed under the hole transport layer 123.

According to an embodiment, when the hole transport layer 123 is formed between the perovskite light absorption layer 124 and the second electrode 126, the perovskite light absorption layer 124 may be formed under the first electrode 122.

The perovskite light absorption layer 124 generates electron-hole pairs by visible light that passes through the first electrode 122 and is incident on the perovskite light absorption layer 124.

The amount of electrons-holes pairs may vary depending upon the amount of energy of visible light absorbed by the perovskite light absorption layer 124.

The perovskite light absorption layer 124 according to an embodiment of the present invention may include a perovskite compound.

The perovskite compound included in the perovskite light absorption layer 124 is a material capable of absorbing visible light incident through the first electrode 122 and converting the absorbed visible light into an electrical signal, and may include a perovskite compound having a perovskite structure.

The perovskite light absorption layer 124 may can control a region that can maximally absorb light according to the structure and composition ratio of the perovskite compound, and when the amount of light absorption increases, the amount of converted electron-hole pairs also increases.

In addition, when both the scintillator 110 and the perovskite light absorption layer 124 are fabricated using a perovskite compound, the perovskite photodetector 120 may be fabricated to maximally absorb light in an emitted region, so that the high efficiency of the perovskite X-ray detector 100 may be maximized.

The perovskite compound included in the perovskite light absorption layer 124 may be represented by Formula 1 as in the perovskite compound included in the scintillator 110. Description of the perovskite compound has been provided upon the description of the scintillator 110, and thus, a redundant description thereof is omitted.

According to an embodiment, the perovskite compound included in the perovskite light absorption layer 124 may be the same as or different from the perovskite compound included in the scintillator 110.

For example, the perovskite compound included in the scintillator 110 may be $CsPbBr_3$, and the perovskite compound included in the perovskite light absorption layer 124 may be $MAPbI_3$.

In addition, since the perovskite light absorption layer 124 may include two or more perovskite compounds, the perovskite photodetector 120 may be fabricated to have excellent efficiency not only in the wavelength band of 550 nm but also in other wavelength bands by the perovskite compounds of various structures and composition ratios.

According to an embodiment, the perovskite light absorption layer 124 may be fabricated in the form of a thin film.

Particularly, the perovskite light absorption layer 124 may be formed to a thickness of 10 nm to 200 µm, preferably 100 nm to 1 µm.

When the thickness of the perovskite light absorption layer 124 exceeds 200 µm, a voltage for reaching the electron-hole pairs, converted in the perovskite light absorption layer 124, to the second electrode 126 or the substrate 121 increases, and there is a risk of peeling due to a decrease in adhesive strength to the substrate 121.

In addition, when the thickness of the perovskite light absorption layer 124 is less than 10 nm, the amount of light absorbed by the scintillator 110 is small, so that a signal is weakened to a noise level.

Since the perovskite light absorption layer 124 is formed to include a perovskite compound, a trap density is small. Accordingly, charges generated in the perovskite light absorption layer 124 may smoothly move to the second electrode 126 without being trapped in a trap.

The electron transport layer 125 is formed under the perovskite light absorption layer 124 and, particularly, is formed between the perovskite light absorption layer 124 and the second electrode 126.

According to an embodiment, the electron transport layer 125 may be formed between the first electrode 122 and the perovskite light absorption layer 124, or may be formed both between the first electrode 122 and the perovskite light absorption layer 124 and between the second electrode 126 and the perovskite light absorption layer 124.

For example, when the electron transport layer 125 is formed between the first electrode 122 and the perovskite light absorption layer 124, the hole transport layer 123 may be formed between the perovskite light absorption layer 124 and the second electrode 126.

Conversely, when the hole transport layer 123 is formed between the first electrode 122 and the perovskite light absorption layer 124, the electron transport layer 125 may be formed between the perovskite light absorption layer 124 and the second electrode 126.

The electron transport layer 125 allows electrons generated in the perovskite light absorption layer 124 to smoothly move to the first electrode 122 and/or the second electrode 126, thereby being capable of reducing dark current.

The electron transport layer 125 may be formed to include, for example, titanium oxide ($TiO_x$), zinc oxide ($ZnO_x$), indium oxide ($InO_x$), tin oxide ($SnO_x$), tungsten oxide ($WO_x$), niobium oxide ($NbO_x$), molybdenum oxide ($MoO_x$), magnesium oxide ($MgO_x$), zirconium oxide ($ZrO_x$), strontium oxide (SrOx), lanthanum oxide (LaOx), vanadium oxide ($VO_x$), aluminum oxide ($AlO_x$), yttrium oxide ($YO_x$), scandium oxide ($ScO_x$), gallium oxide ($GaO_x$), indium oxide ($InO_x$), or a mixture or composite thereof.

In addition, the electron transport layer 125 may include at least one of fullerene (C60), a fullerene derivative, perylene, TPBi (2,2',2''-(1,3,5-benzinetriyl)-tris (1-phenyl-1-H-benzimidazole)), PBI (polybenzimidazole) and PTCBI (3,4,9,10-perylene-tetracarboxylic bis-benzimidazole), NDI (Naphthalene diimide) and a derivative thereof, $TiO_2$, $SnO_2$, ZnO, $ZnSnO_3$, 2,4,6-Tris (3-(pyrimidin-5-yl)phenyl)-1,3,5-triazine, 8-Hydroxyquinolinolato-lithium, 1,3,5-Tris (1-phenyl-1Hbenzimidazol-2-yl)benzene, 6,6'-Bis[5-(biphenyl-4-yl)-1,3,4-oxadiazo-2-yl]-2,2'-bipyridyl, 4,4'-Bis (4,6-diphenyl-1,3,5-triazin-2-yl)biphenyl (BTB), $Rb_2CO_3$ (Rubidium carbonate), and $ReO_3$ (Rhenium (VI) oxide), and the fullerene derivative may be PCBM ((6,6)-phenyl-C61-butyric acid-methylester) or PCBCR ((6,6)-phenyl-C61-butyric acid cholesteryl ester), without being limited thereto.

The electron transport layer 125 may be formed by various solution coating methods using solutions, or various deposition methods.

The solution coating method may be, for example, spin coating, spray coating, ultra-spray coating, electrospinning coating, slot die coating, gravure coating, bar coating, roll coating, dip coating, shear coating, screen printing, inkjet printing, nozzle printing, or the like.

The deposition method may be, for example, sputtering, atomic layer deposition, chemical vapor deposition, thermal evaporation, co-evaporation, plasma enhanced chemical vapor deposition, or the like under a reduced pressure condition, an atmospheric pressure condition or a pressurized condition.

The electron transport layer 125 serves to move electrons to the perovskite light absorption layer 124, allows electrons to be effectively transferred to the perovskite light absorption layer 124, and may improve efficiency by balancing the densities of holes and electrons in the perovskite light absorption layer 124.

The second electrode 126 is formed under the electron transport layer 125.

According to an embodiment, the second electrode 126 may be formed under the hole transport layer 123 when the hole transport layer 123 is formed between the perovskite light absorption layer 124 and the second electrode 126.

According to an embodiment, the second electrode 126 may be made of a conductive material having excellent electrical characteristics.

The second electrode 126 may be formed to include, for example, aluminum (Al), at least one selected from the group consisting of silver (Ag), gold (Au), copper (Cu), palladium (Pd), platinum (Pt), indium tin oxide (ITO), indium zinc oxide (IZO), aluminum zinc oxide (AZO), fluorine tin oxide (FTO), carbon nano tube (CNT, Carbon Nano Tube), graphene and polyethylenedioxythiophene:polystyrenesulfonate (PEDOT:PSS).

Alternatively, the second electrode 126 may be, without being limited to, lithium fluoride/aluminum (LiF/Al), cobalt sulfide (CoS), copper sulfide (CuS), nickel oxide (NiO) or a mixture thereof.

The second electrode 126 may be formed by the method described regarding the first electrode 122, and thus, a redundant description thereof is omitted.

Hereinafter, an operation principle of the perovskite X-ray detector 100 including the perovskite photodetector 120 according to an embodiment of the present invention is described.

X-rays incident on the scintillator 110 from the outside are converted into visible light in the scintillator 110, and the visible light converted in the scintillator 110 passes through the first electrode 122 of the perovskite photodetector 120 and then, is absorbed by the perovskite light absorption layer 124, so that electrons-holes pairs are generated in the perovskite light absorption layer 124.

The electrons-holes pairs generated in the perovskite light absorption layer 124 are separated by a potential difference due to a voltage applied to the first electrode 122 and the second electrode 126 and respectively move to the first electrode 122 and the second electrode 126.

For example, when a negative (−) voltage is applied to the first electrode 122, holes generated in the perovskite light absorption layer 124 move to the first electrode 122, and electrons move to the second electrode 126.

On the other hand, when a positive (+) voltage is applied to the first electrode 122, electrons generated in the perovskite light absorption layer 124 move to the first electrode 122, and holes move to the second electrode 126.

The hole transport layer 123 and the electron transport layer 125 contribute to smooth movement of the electrons and holes generated in the perovskite light absorption layer 124 to the first electrode 122 or the second electrode 126.

Charges (electrons or holes) moved to the first electrode 122 are stored in a capacitor (not shown) formed in the substrate 121. Since charges are stored in the capacitor, X-ray detection voltage may be stored.

That is, as X-rays are irradiated to the scintillator 110, a predetermined voltage is formed in the capacitor, and the predetermined voltage applied to the capacitor varies according to the amount of X-rays irradiated to the scintillator 110. This predetermined voltage may be read as an electrical signal by operation of a thin film transistor (TFT) (not shown) formed on the substrate 121.

Particularly, when the thin film transistor is turned on by inputting an electrical signal to the thin film transistor formed on the substrate 121, the charges stored in the capacitor are transmitted to a signal processor (not shown) through a drain electrode of the thin film transistor, and the signal processor may measure the X-ray transmittance of a measurement target object based on the amount of charges.

Since the perovskite light absorption layer 124 of the perovskite photodetector 120 according to an embodiment of the present invention includes a perovskite compound, the perovskite photodetector 120 according to an embodiment of the present invention may respond very sensitively to a minute light intensity, so that light may be detected with high responsivity.

As criteria for determining the sensitivity of the perovskite photodetector 120 according to an embodiment of the present invention, responsivity and specific detectivity may be used. The responsivity of the perovskite photodetector 120 may be calculated through Equation 1 below.

$$R=(J_{ph}-J_d)/P \qquad \text{[Equation 1]}$$

where R denotes a responsivity, $J_{ph}$ denotes a photocurrent density, $J_d$ denotes a dark current density, and P denotes a transient light intensity.

The responsivity of the perovskite photodetector 120 according to an embodiment of the present invention calculated according to Equation 1 may be 0.0001 A/W to 1A/W.

When the responsivity is less than 0.0001 A/W, the number of charges generated in the perovskite photodetector 120 is small, so that detection is difficult.

Since the perovskite X-ray detector 100 according to an embodiment of the present invention does not require an external power source, the perovskite photodetector 120 may have a responsivity of up to 1 A/W.

In addition, the specific detectivity of the perovskite photodetector 120 may be calculated through Equation 2 below.

$$D^*=RA^{0.5}S_n^{-1} \qquad \text{[Equation 2]}$$

where $D^*$ denotes a specific detectivity, R denotes a responsivity, A denotes a light sensing area, and Sn denotes a noise spectral density.

The specific detectivity of the perovskite photodetector 120 according to an embodiment of the present invention calculated according to Equation 2 may be $10^9$ cmHz$^{0.5}$/W to $10^{13}$ cmHz$^{0.5}$/W.

A reaction time of the perovskite photodetector 120 may be known based on the responsivity and the specific detectivity of the perovskite photodetector 120.

Accordingly, the reaction time of the perovskite photodetector 120 may be 0.01 μs to 100 μs.

When the reaction time of the perovskite photodetector 120 exceeds 100 μs, an afterimage is generated due to the overlap of signals when an image such as a moving image with a fast response speed is obtained. When the reaction time is less than 0.01 μs, charges generated by the perovskite photodetector 120 the does not require an external power source are accelerated and thus cannot be extracted, so that there is difficulty in implementing.

Since the perovskite X-ray detector 100 according to an embodiment of the present invention has a combined form of the scintillator 110 and the perovskite photodetector 120, the scintillator 110 having excellent PL lifespan and the perovskite photodetector 120 having excellent responsivity and specific detectivity create a synergistic effect to have a high current density and excellent X-ray sensitivity.

Particularly, the current density of the perovskite X-ray detector 100 may be 0.00001 mA/cm$^2$ to 10 mA/cm$^2$.

According to an embodiment, a current density value and an X-ray sensitivity value may be changed according to a tube current or tube voltage applied to the perovskite X-ray detector 100.

Particularly, when the tube current value of the perovskite X-ray detector 100 is fixed, a current density may increase in proportion to a tube voltage and, when the tube voltage thereof is fixed, a current density may increase in proportion to a tube current.

More particularly, the perovskite X-ray detector 100 may have a current density of 0.017 mA/cm$^2$ to 0.199 mA/cm$^2$ when the tube current is 1 mA and the tube voltage is changed from 30 keV to 120 keV.

In addition, the perovskite X-ray detector 100 may have a current density of 0.041 mA/cm$^2$ to 0.174 mA/cm$^2$ when the tube voltage is 90 keV and the tube current is changed from 0.25 mA to 1 mA.

The X-ray sensitivity of the perovskite X-ray detector 100 according to an embodiment of the present invention may be calculated based on a current density according to X-ray radiation, an X-ray dose and the thickness of an active region, and may be expressed by Equation 3 below.

$$S=[\int(J_{x\text{-}ray}(t)-J_{dark})dt](DA_t)^{-1}$$ [Equation 3]

where S indicates an X-ray sensitivity of the perovskite X-ray detector 100, $J_{x\text{-}ray}$ (t) indicates a current density generated by X-ray radiation for t time, $J_{dark}$ indicates a dark current density in the absence of X-ray radiation, D indicates an X-ray dose, and $A_t$ indicates the thickness of an active region.

Here, the active region means the perovskite X-ray detector 100 to which X-rays are radiated, the thickness of the active region means the thickness of the perovskite X-ray detector 100, the area of the active region means the area of the perovskite X-ray detector 100, and the volume of the active region means the thickness of the perovskite X-ray detector 100, i.e., the product of the area and the thickness of the perovskite X-ray detector.

Here, $A_t$ may be deleted to calculate the X-ray sensitivity (S) of the perovskite X-ray detector 100.

In addition, to calculate the X-ray sensitivity of the perovskite X-ray detector 100, the thickness of an active region, the thickness of the scintillator 110 and the thickness of the perovskite photodetector 120 may be fixed to specific values.

The X-ray sensitivity of the perovskite X-ray detector 100 according to an embodiment of the present invention may be 600 $\mu$CmGy$_{air}^{-1}$ cm$^{-3}$ to 1,270 $\mu$CmGy$_{air}^{-1}$ cm$^{-3}$.

According to an embodiment, when the tube current value of the perovskite X-ray detector 100 is fixed, the X-ray sensitivity may increase in proportion to the tube voltage.

According to the perovskite X-ray detector 100 according to an embodiment of the present invention, the X-ray sensitivity of the perovskite X-ray detector 100 may be 10 $\mu$CmGy$_{air}^{-1}$ cm$^{-2}$ to 1,000 $\mu$CmGy$_{air}^{-1}$ cm$^{-2}$ based on the area of the active region.

In addition, according to the perovskite X-ray detector according to an embodiment of the present invention, the X-ray sensitivity of the perovskite X-ray detector 100 may be 100 $\mu$CmGy$_{air}^{-1}$ cm$^{-3}$ to 10,000 $\mu$CmGy$_{air}^{-1}$ cm$^{-3}$ based on the volume of the active region.

The X-ray sensitivity value of the perovskite X-ray detector 100 based on the volume of the active region may be calculated by dividing the thickness of an active region ($A_t$) by the X-ray sensitivity value of the perovskite X-ray detector 100 based on the area of the active region.

Since the perovskite X-ray detector 100 according to an embodiment of the present invention is a flexible device, the current density and the X-ray sensitivity may be maintained even when the perovskite X-ray detector 100 is repeatedly bent.

Particularly, the performance of the perovskite X-ray detector 100 may be maintained even if the bending operation of bending and unfolding the perovskite X-ray detector 100 is repeated 1000 times.

In addition, the perovskite X-ray detector 100 according to an embodiment of the present invention may maintain the current density and the X-ray sensitivity regardless of a bending radius.

Particularly, the performance of the perovskite X-ray detector 100 may be maintained even when the perovskite X-ray detector 100 is bent to 1 mm to 6 mm.

The scintillator 110 and perovskite photodetector 120 according to the present invention were fabricated according to the following fabrication methods, and then the characteristics and effects of the perovskite X-ray detector 100 were evaluated through the following comparative examples and examples.

FABRICATION EXAMPLE

1. Preparation of CsPbBr$_3$ Nanocrystal 0.814 g of CsPbBr$_3$ (Aldrich, 99.9%) as a perovskite compound and 2.5 ml of oleic acid (OA, Aldrich 90%) were reacted in 40 mL of octadecene (ODE, Aldrich, 90) at 150° C. in a nitrogen atmosphere to prepare a Cs-oleate solution.

Next, 0.069 g of PbBr$_2$ (99.999%, Aldrich), 0.5 mL of oleylamine (OLA, Acros, 80-90%), and 0.5 mL of oleic acid were reacted in 0.5 mL of octadecene at 150° C. for 1 hour in a nitrogen atmosphere to prepare a PbBr$_2$ precursor solution precursor solution.

Next, 0.4 ml of a Cs-oleate solution was rapidly injected into the PbBr$_2$ precursor solution, and the resultant mixture was allowed to react at 150° C. for 10 seconds and then cooled.

After cooling, CsPbBr$_3$ nanocrystals as perovskite nanocrystals separated from the solvent by centrifugation were redispersed in hexane (Aldrich, anhydrous 95%), thereby preparing a CsPbBr$_3$ nanocrystal solution.

2. Fabrication of CsPbBr$_3$ Scintillator

A PDMS monomer (SYLGARD 184A, SEWANG HITECH CO. LTD.) and a curing agent (SYLGARD 184B, SEWANG HITECH CO. LTD.) were mixed in a weight ratio of 10:1.

Next, 1 mL of CsPbBr$_3$ nanocrystal solution (CsPbBr$_3$ nanocrystal at a concentration of about 0.5 g/mL) was added to the PDMS monomer/curing agent mixture.

Next, air bubbles and the solvent were removed from the mixture in a vacuum oven for 1 hour.

The mixture from which air bubbles and the solvent had been removed was poured onto a glass substrate, followed by being spin-coated at 500 rpm for 60 seconds.

After the spin coating, polymerization was performed at 60° C. for 12 hours under a nitrogen condition, thereby fabricating a CsPbBr$_3$ scintillator.

3. Fabrication of MAPbI$_3$ Perovskite Photodetector

First, a filtered PEDOT:PSS (Clevios, Al4083)/methanol mixture (volume ratio of 1:2) was spin-coated on a indium tinoxide (ITO) PET substrate at 3000 rpm for 60 seconds, followed by drying at 150° C. for 20 minutes. As a result, a hole transport layer was formed.

Next, 40% by weight of a MAPbI$_3$/DMF (N,N-dimethylformamide, Aldrich, 99%) solution (40% by weight of MAPbI$_3$ in DMF solution/hydroiodic acid mixed in a ratio of 1 mL/100 μL) to which a hydroiodic acid additive has been added was spin-coated on PEDOT:PSS as a hole transport layer at 3000 rpm for 200 seconds, followed by drying on a hot plate at 100° C. for 2 minutes. As a result, a perovskite light absorption layer including MAPbI$_3$ was formed.

A PCBM (Phenyl-C61-butyricacid methyl ester)/toluene (20 mg/1 mL) solution was spin-coated on the perovskite light absorption layer at 2000 rpm for 60 seconds, so that an electron transport layer was deposited on the perovskite light absorption layer.

Finally, aluminum (Al) was formed by thermal deposition on the electron transport layer.

Example 1

A flexible perovskite X-ray detector manufactured by positioning the perovskite photodetector such that a substrate contacted a lower surface of the scintillator according to the fabrication example.

Example 2

A non-flexible perovskite X-ray detector manufactured to include a scintillator and perovskite photodetector manufactured in the same manner as in the fabrication example except that a substrate of the perovskite photodetector was a glass substrate.

The flexible perovskite X-ray detector according to the present invention includes a scintillator and a perovskite photodetector, and thus, may exhibit the characteristics of the scintillator and the perovskite photodetector.

Accordingly, the characteristic evaluation of the scintillator and the perovskite photodetector was respectively performed, and then the characteristic evaluation of the flexible perovskite X-ray detector was performed.

Characteristic Evaluation

1. Characteristic Evaluation of $CsPbBr_3$ Scintillator

FIG. 3 illustrates an electron transmission microscope (TEM) image of a scintillator according to an embodiment of the present invention and the emission state of the scintillator according to irradiation light.

Referring to FIG. 3, it can be confirmed that the synthesized $CsPbBr_3$ perovskite nanocrystals are uniformly dispersed in the shape of nanocubes or nanobars with a size of ~10 nm.

Referring to TEM images inserted in FIG. 3, it can be confirmed that the $CsPbBr_3$ perovskite nanocrystals have a cubic crystal structure exposing facets {100}.

FIG. 4 illustrates an X-ray diffraction (XRD) pattern of a scintillator according to an embodiment of the present invention.

Referring to FIG. 4, it can be confirmed that synthesized $CsPbBr_3$ perovskite nanocrystals have a cubic phase consistent with the TEM image of FIG. 3 described above.

FIG. 5 illustrates UV-visible and photoluminescence (PL) spectra of a scintillator according to an embodiment of the present invention.

In FIG. 5, the green line represents a UV-visible light absorption spectrum, and an orange line represents a photoluminescence spectrum.

Referring to FIG. 5, it can be confirmed that the $CsPbBr_3$ perovskite nanocrystals have an on-set absorption band edge at a wavelength of ~510 nm, and a strong single PL peak with a line width of about 20 nm at a wavelength of ~520 nm.

FIG. 6 illustrates a transient PL decay curve of a scintillator according to an embodiment of the present invention.

In FIG. 6, an IRF graph represents the peak of laser irradiated to the scintillator according to an embodiment of the present invention.

Referring to FIG. 6, it can be confirmed that the average PL lifespan of the $CsPbBr_3$ perovskite nanocrystals is 2.81 ns ($\tau_1$=0.42 ns (48.77%), $\tau_2$=5.16 ns (51.23%)).

Here, $\tau_1$ denotes an exciton lifetime associated with a fast decay in which excitons directly emit light, and $\tau_2$ denotes an exciton lifetime associated with a slow decay.

Referring to FIG. 3 again, it can be confirmed that, as observation results of the $CsPbBr_3$ scintillators irradiated with room light and X-ray (90 keV, 1 mA), the $CsPbBr_3$ scintillator irradiated with room light shows relatively weak PL radiation, but the $CsPbBr_3$ scintillator irradiated with X-ray shows strong cyan PL radiation.

This indicates that the $CsPbBr_3$ perovskite nanocrystals can emit PL even by a low X-ray dose. A flexible perovskite X-ray detector including such a scintillator can detect X-rays very sensitively.

Hereinafter, X-ray intensity was measured so as to evaluate the response characteristics of the scintillator of the example with respect to the X-ray tube current and the tube current.

FIG. 7 illustrates the X-ray dose rate and transmittance according to a tube current of a scintillator according to an embodiment of the present invention.

Here, the transmittance means an intensity ratio of X-rays irradiated to the scintillator to X-rays that have passed through the scintillator.

Referring to FIG. 7, it can be confirmed that when the tube voltage is fixed at 90 keV, the dose rate linearly increases as the tube current increases, but the transmittance of the $CsPbBr_3$ scintillator slightly increases as the tube current increases.

FIG. 8 illustrates the X-ray dose rate and transmittance according to a tube voltage of a scintillator according to an embodiment of the present invention.

Referring to FIG. 8, it can be confirmed that when the tube current is fixed to 1 mA, the dose rate rapidly increases as the tube voltage increases, and the transmittance of the $CsPbBr_3$ scintillator also significantly increases as the tube voltage increases.

The contrasting results of FIGS. 7 and 8 are because X-rays generated by the fixed tube voltage have similar X-ray photon energy and thus have similar absorbance regardless of the number of X-ray photons with similar X-ray photon energy.

FIG. 9 illustrates X-ray photon energy-dependent mass attenuation of a scintillator according to an embodiment of the present invention and perovskite photodetector.

Referring to FIG. 9, it can be confirmed that, as a result of observing a change in mass attenuation according to the X-ray photon energy regarding X-rays generated by the fixed tube current, the mass attenuation tends to decrease as the X-ray photon energy increases.

From the result, it can be confirmed that a similar number of X-ray photons with gradually higher X-ray photon energy is emitted as the tube voltage increases, so that mass attenuation gradually decreases and thus an absorbance decreases. In addition, it can be confirmed that the dose rate of the X-rays generated by the fixed tube current rapidly increases as the tube voltage increases.

FIG. 10 illustrates a PL spectrum according to a tube current when a tube voltage of a scintillator according to an embodiment of the present invention is 90 keV.

Referring to FIG. 10, it can be confirmed that in all of tube currents of 0.25 mA, 0.5 mA, 0.75 mA and 1 mA, green light has strong emission at a wavelength of ~533 nm.

In addition, it can be confirmed that the PL intensity of the scintillator increases as the tube current increases at the fixed tube voltage.

FIG. 11 illustrates a PL spectrum according to a tube voltage when a tube current of a scintillator according to an embodiment of the present invention is 1 mA.

Referring to FIG. 11, it can be confirmed that in all of tube currents of 30 keV, 60 keV, 90 keV and 120 keV, green light has strong emission at a wavelength of ~533 nm.

In addition, it can be confirmed that the PL intensity of the scintillator increase as the tube voltage increases at the fixed tube current.

From the above results of FIGS. 10 and 11, it can be confirmed that the PL intensity depends upon the dose rate of X-rays irradiated to the scintillator.

This means that the $CsPbBr_3$ scintillator may respond to a broad X-ray photon energy spectrum and may respond linearly to an X-ray dose rate.

Hereinafter, to confirm the flexibility and flexible durability of the scintillator according to the example, PL intensity according to a bending radius and a bending repetition number was measured while the scintillator was bent.

FIG. 12 illustrates PL intensity according to a bending radius of a scintillator according to an embodiment of the present invention.

FIG. 12 illustrates the PL intensity of the scintillators having bending radii (R) of co (flat state), 6 mm, 4 mm and 2 mm under exposure to X-rays (tube voltage=90 keV, tube current=1 mA).

Here, the bending radius means the radius of curvature with respect to the outer circumferential surface of the scintillator when the scintillator is bent.

Considering that the thickness of the scintillator according to the example is 1.5 mm, it can be confirmed that the bending radius of an inner circumferential surface of the curved scintillator is much smaller than the bending radius of an outer circumferential surface thereof.

Referring to FIG. 12, it can be confirmed that the bent scintillator exhibits similar PL intensity regardless of a bending radius.

That is, since the scintillator according to the example includes PDMS as a flexible polymer, it may have a constant PL intensity when bent.

Accordingly, it can be confirmed that the scintillator according to the example has excellent flexibility.

FIG. 13 illustrates PL intensity of a scintillator according to an embodiment of the present invention according to the number of repeated bending.

Here, an operation of bending and unfolding the scintillator is regarded as one bending count.

Referring to FIG. 13, it can be confirmed that in all of bending radii (R) of 6 mm, 4 mm and 2 mm, the PL intensity values are almost similar.

Particularly, the scintillator of the example may constantly maintain PL strength even when the number of bending times exceeds 1000.

Accordingly, it can be confirmed that the scintillator according to the example has excellent flexible durability while maintaining PL intensity without decrease in PL intensity even when the bending operation is repeated 1000 or more times.

To confirm the stability of the scintillator according to the example, the scintillator was stored for 15 days under an ambient condition and PL intensity thereof was measured every day. Results are shown in the accompanying FIG. 14.

FIG. 14 illustrates PL intensity according to the number of days of use of a scintillator according to an embodiment of the present invention.

Referring to FIG. 14, it can be confirmed that the scintillator according to the example exhibits almost the same PL intensity for 15 days.

This is because the perovskite nanocrystals made of $CsPbBr_3$ as a perovskite compound formed of an inorganic material are immobilized by a long-chain alkyl ligand and mixed with hydrophobic PDMS.

Accordingly, it can be confirmed that the scintillator according to the example has excellent stability.

FIG. 15 illustrates PL intensity according to X-ray exposure of a scintillator according to an embodiment of the present invention.

Referring to FIG. 15, it can be confirmed that the scintillator according to the example maintains the initial PL intensity at an X-ray dose of $70Gy_{air}$.

That is, it can be confirmed that the PL intensity of the scintillator according to the example is almost constant as an X-ray dose increases.

Accordingly, it can be confirmed that the PL intensity of the scintillator according to the example is almost constantly maintained regardless of the X-ray dose, and thus, the scintillator has excellent durability.

2. Characteristic Evaluation of $MAPbI_3$ Perovskite Photodetector

FIG. 16 illustrates a scanning electron microscope (SEM) image of a cross-section of a non-flexible perovskite photodetector according to an embodiment of the present invention.

Referring to FIG. 16, it can be confirmed that, in the case of the non-flexible perovskite photodetector, ITO as a first electrode was formed to a thickness of ~150 nm, PEDOT: PSS as a hole transport layer was formed to a thickness of ~50 nm, a perovskite light absorption layer including MAPbI~3 was formed to a thickness of ~400 nm, PCBM as an electron transport layer was formed to a thickness of ~50 nm, and Al as a second electrode was formed to a thickness of ~50 nm.

FIG. 17 illustrates a current density-voltage (J-V) curve according to light intensity of a non-flexible perovskite photodetector according to an embodiment of the present invention.

FIG. 17 illustrates a current density-voltage curve of the non-flexible perovskite photodetector of Example 2 when light intensity is 1 $\mu W/cm^2$, 5 $\mu W/cm^2$, 10 $\mu W/cm^2$, 50 $\mu W/cm^2$, 100 $\mu W/cm^2$, 500 $\mu W/cm^2$, and 1 $mW/cm^2$.

Here, the light intensity was adjusted from 1 $\mu W/cm^2$ to 1 $mW/cm^2$ with a laser having a wavelength of 510 nm.

Referring to FIG. 17, it can be confirmed that the current density at the zero bias potential gradually increases as the intensity of the irradiated light increases.

FIG. 18 illustrates responsivity and specific detectivity according to light intensity of a non-flexible perovskite photodetector according to an embodiment of the present invention.

Referring to FIG. 18, it can be confirmed that although the non-flexible perovskite photodetector of Example 2 has various light intensities, the responsivity (R) and the specific detectivity (D*) are slightly decreased and almost constant.

Specific values of the responsivity and specific detectivity of the non-flexible perovskite photodetector of Example 2 are described below with reference to FIG. 19.

FIG. 19 illustrates a noise spectral density according to a frequency of a non-flexible perovskite photodetector according to an embodiment of the present invention.

Referring to FIG. 19, it can be confirmed that the non-flexible perovskite photodetector of Example 2 has a noise spectral density (Sn) of ~$4.0 \times 10^{12}$ $AHz^{-0.5}$.

From the above results of FIGS. 17 and 19 and Equations 1 and 2, it can be confirmed that the non-flexible perovskite photodetector of Example 2 has a responsivity of ~0.35 A/W and a specific detectivity of ~$2.4 \times 10^{12}$ $cmHz^{0.5}/W$.

FIG. 20 illustrates a linear dynamic range (LDR) of a non-flexible perovskite photodetector according to an embodiment of the present invention.

Referring to FIG. 20, a plot of the log value of the current density and the log value of the light intensity confirms that the linear dynamic range (LDR) of the non-flexible perovskite photodetector of Example 2 is ~158 dB.

FIG. 21 illustrates signal attenuation according to a frequency of a non-flexible perovskite photodetector according to an embodiment of the present invention.

Here, the y-axis of FIG. 21 represents a signal attenuation amount (10 log (I/I$_0$)).

Referring to FIG. 21, it can be confirmed that the 3 dB penalty frequency of the non-flexible perovskite photodetector of Example ~2 is ~5 MHz.

This indicates that the non-flexible perovskite photodetector of Example 2 may process information up to a frequency level of MHz.

To confirm that the non-flexible perovskite photodetector of Example 2 can process information up to a frequency level of MHz, a signal of 1 MHz was collected through the non-flexible perovskite photodetector of Example 2, which is described below with reference to the accompanying FIG. 22.

FIG. 22 illustrates an output photocurrent signal in a 1 MHz input pulse modulation of a non-flexible perovskite photodetector according to an embodiment of the present invention.

Referring to the enlarged image inserted in FIG. 22, it can be confirmed that a rise time (t$_r$) and decay time (t$_d$) of a response signal of the non-flexible perovskite photodetector of Example 2 from the signal collected from the non-flexible perovskite photodetector of Example 2 are respectively 0.30 μs and 0.31 μs.

Accordingly, the non-flexible perovskite photodetector of Example 2 may effectively acquire information in real time.

So far, the response characteristics and signal detection characteristics of the non-flexible perovskite photodetector according to Example 2 were evaluated.

Since the perovskite photodetector according to the present invention has flexibility and can be fabricated only by imparting flexibility to a non-flexible perovskite photodetector, the perovskite photodetector may have both the response characteristics and signal detection characteristics of a non-flexible perovskite photodetector.

Accordingly, it can be seen that the flexible perovskite photodetector according to Example 1 also has very excellent response characteristics and signal detection characteristics referring to the characteristic evaluation of the non-flexible perovskite photodetector of Example 2 described above.

Hereinafter, the flexible characteristics (flexibility, flexible durability, stability) of the flexible perovskite photodetector of Example 1 having flexibility, unlike the non-flexible perovskite photodetector of Example 2 are evaluated.

FIG. 23 illustrates a bent state of a flexible perovskite photodetector according to an embodiment of the present invention.

Referring to FIG. 23, the flexible perovskite photodetector of Example 1 was composed of PET substrate/ITO/PEDOT:PSS/MAPbI$_3$/PCBM/Al according to the fabrication example, and the size of the flexible perovskite photodetector is 2.54×2.54 cm$^2$, and each active region thereof is 0.16 cm$^2$.

In addition, it can be confirmed from FIG. 23 that the flexible perovskite photodetector of Example 1 has flexibility that can be easily bent when an external force is applied.

FIG. 24 illustrates a current density-voltage curve according to a bending radius of a flexible perovskite photodetector according to an embodiment of the present invention.

Here, FIG. 24 illustrates J-V curves of the flexible perovskite photodetectors of Example 1 bent to have bending radii of ∞ (flat state), 6 mm, 4 mm and 2 mm in the dark and in the present of light of 1 mW/cm$^2$.

Referring to FIG. 24, it can be confirmed that the current density and dark current density of the flexible perovskite photodetector of Example 1 are almost constant regardless of the bending radius.

Accordingly, it can be confirmed that the flexible perovskite photodetector of Example 1 may collect a specific information signal without distortion even in an environment bent by an external force.

FIG. 25 illustrates a current density of a flexible perovskite photodetector according to an embodiment of the present invention when repeatedly bent.

Referring to FIG. 25, the current density (J$_{ph}$) of the flexible perovskite photodetector of Example 1 which was repeatedly bent is almost constant regardless of the number of bending, but dark current density (J$_d$) of the flexible perovskite photodetector increases as the number of bending increases.

In addition, it can be confirmed that a reduction amount in dark current density of the flexible perovskite photodetector of Example 1 increases as the bending radius decreases.

FIG. 26 illustrates responsivity to repetitive bending of a flexible perovskite photodetector according to an embodiment of the present invention.

FIG. 26 illustrates the responsivity (R) according to the number of bending when the flexible perovskite photodetectors of Example 1 were bent to have bending radii of 6 mm, 4 mm, and 2 mm, respectively, and images showing bending of the flexible perovskite photodetector of Example 1 were inserted into the graph of FIG. 26.

Referring to FIG. 26, it can be confirmed that the responsivity of the flexible perovskite photodetector of Example 1 having the same bending radius is almost constant up to 1000 bending times.

Since the responsivity is a function of a current density, dark current density and transient light intensity as can be seen from Equation 1, the responsivity is also almost constant because the current density with respect to the number of bending is almost constant as described above with reference to FIG. 25.

In addition, referring to FIG. 26, it can be seen that when the bending radius of the flexible perovskite photodetector of Example 1 is reduced for the same number of bending, the responsivity is also slightly lowered.

This is because the dark current density increases as the bending radius according to FIG. 25 decreases.

That is, according to Equation 1, it can be seen that the responsivity of the flexible perovskite photodetector of Example 1 is decreased because the dark current density increases.

However, even considering that the responsivity decreases as the bending radius decreases, the responsivity of the flexible perovskite photodetector of Example 1 shows an almost constant level without a sharp change, which informs that the flexible durability and stability are excellent.

Accordingly, it can be seen that the flexible perovskite photodetector according to an embodiment of the present invention has flexibility, flexible durability and stability while having excellent response characteristics and signal detection characteristics.

3. Characteristic Evaluation of Perovskite X-Ray Detector

FIG. 27 illustrates a current density according to a change in each of the tube current and tube voltage of a non-flexible perovskite X-ray detector according to an embodiment of the present invention.

FIG. 27 illustrates results obtained by performing the same experiments as those of FIGS. 7 and 8 related to the non-flexible perovskite X-ray detector of Example 2.

Referring to FIG. 27, the non-flexible perovskite X-ray detector of Example 2 showed the same reaction as that of the scintillator of Example 2 because the Si photodetector used in the experiments of FIGS. 7 and 8 was replaced with a perovskite photodetector.

It can be confirmed that the current density of the non-flexible perovskite X-ray detector of Example 2 linearly increases as the tube current and the tube voltage increase.

At the tube current fixed to 1 mA, it can be confirmed that the current density of the non-flexible perovskite X-ray detector of Example 2 increases from 0.017 mA/cm$^2$ to 0.199 mA/cm$^2$ as the tube voltage increases from 30 keV to 120 keV.

In addition, at the tube voltage fixed to 90 keV, it can be confirmed that the non-flexible perovskite X-ray detector of Example 2 shows a current density of 0.041 mA/cm$^2$ to 0.174 mA/cm$^2$ as the tube current increases from 0.25 mA to 1 mA.

FIG. 28 illustrates X-ray sensitivity according to a change in each of a tube current and a tube voltage of a non-flexible perovskite X-ray detector according to Example 2 of the present invention.

Here, the area of an active region, the thickness of the scintillator of Example 2 and the thickness of the perovskite photodetector of Example 2 were respectively fixed to 0.16 cm$^2$, 0.15 cm and 4×10$^{-5}$ cm, and then X-ray sensitivity of the non-flexible perovskite X-ray detector of Example 2 were calculated through Equation 3.

Referring to FIG. 28, it can be confirmed that, when a tube current is changed from 0.25 mA to 1 mA at a fixed tube voltage of 90 keV, the X-ray sensitivity of Example 2 is ~140 μCm/Gy$_{air}$ cm$^3$ based on an active region and ~960 μCm/Gy$_{air}$ cm$^3$ based on an active volume.

In addition, it can be confirmed that when the tube voltage is 30 keV to 120 keV at a fixed tube current of 1 mA, the X-ray sensitivity of Example 2 is 100 μCm/Gy$_{air}$ cm$^3$ to 210 μCm/Gy$_{air}$ cm$^3$ based on an active region and 650 μCm/Gy$_{air}$ cm$^3$ to 1370 μCm/Gy$_{air}$ cm$^3$ based on an active volume.

The reason that the non-flexible perovskite X-ray detector of Example 2 has constant X-ray sensitivity under the fixed tube voltage regardless of a change in the tube current is due to the constant absorption rate of the scintillator shown in FIG. 7 described above.

On the other hand, the increase in X-ray sensitivity according to the increase in the tube voltage under the fixed tube current of the non-flexible perovskite X-ray detector of Example 2 is due to the increase in the absorption rate of the scintillator according to the dose rate.

FIG. 29 illustrates an output signal when an X-ray input signal is applied at 50 ms intervals to a non-flexible perovskite X-ray detector according to Example 2 of the present invention.

Referring to FIG. 29, it can be confirmed that there is no time delay an output signal when an X-ray input signal having a time interval of 50 ms is irradiated to the non-flexible perovskite X-ray detector of Example 2.

Such fast response of the perovskite X-ray detector is due to a very short transient PL average lifespan (2.81 ns) of the scintillator and a fast reaction time (~0.3 μs) of the non-flexible perovskite photodetector of Example 2.

FIG. 30 illustrates a current density according to a change in each of a tube current and a tube voltage of a flexible perovskite X-ray detector according to an embodiment of the present invention.

FIG. 30 illustrates measurement results of the current density of the flexible perovskite X-ray detector of Example 1 under the same experimental conditions as in FIG. 27 described above.

Referring to FIG. 30, it can be confirmed that the flexible perovskite X-ray detector of Example 1 has the same current density characteristics as those of the non-flexible perovskite X-ray detector of Example 2 as described above with reference to FIG. 27.

That is, it can be confirmed that the current density of the flexible perovskite X-ray detector of Example 1 linearly increases as the tube current and the tube voltage increase.

It can be confirmed that as the current density tendency of the flexible perovskite X-ray detector of Example 1 is similar to that of the non-flexible perovskite X-ray detector of Example 2, the X-ray sensitivity tendency of the flexible perovskite X-ray detector of Example 1 is also similar to the X-ray sensitivity tendency of Example 2. This is described below with reference to FIG. 31.

FIG. 31 illustrates X-ray sensitivity according to a change in each of a tube current and a tube voltage of a flexible perovskite X-ray detector according to an embodiment of the present invention.

Referring to FIG. 31, it can be confirmed that the X-ray sensitivity tendency of the flexible perovskite X-ray detector of Example 1 is similar to the X-ray sensitivity tendency of Example 2.

That is, it can be confirmed that, when the tube current is changed from 0.25 mA to 1 mA at a fixed tube voltage of 90 keV, the X-ray sensitivity of Example 1 is ~130 μCm/Gy$_{air}$ cm$^3$ based on an active region and ~870 μCm/Gy$_{air}$ cm$^3$ based on an active volume.

In addition, it can be confirmed that when the tube voltage is 30 keV to 120 keV at a fixed tube current of 1 mA, the X-ray sensitivity is 90 μCm/Gy$_{air}$ cm$^3$ to 190 μCm/Gy$_{air}$ cm$^3$ based on an active region and 600 μCm/Gy$_{air}$ cm$^3$ to 1270 μCm/Gy$_{air}$ cm$^3$ based on an active volume.

Examples 1 and 2 have different X-ray sensitivity values, which is because the intensity of light emitted from the scintillator is the same, but the amount of light entering the perovskite photodetector in the glass substrate (Example 2) and the amount of light entering the perovskite photodetector in the plastic (PET) substrate (Example 1) are different.

Particularly, since glass, which is the substrate material of Example 2, has a refractive index of 1.51, a PET, which is the substrate material of Example 1, has a refractive index of about 1.7, and a lot of reflection occurs on the PET substrate, the amount of light entering the perovskite photodetector of Example 1 is small, so that the X-ray sensitivity of Example 1 is small compared to that of Example 2 using a glass substrate.

In the case of Example 1, the problem of the flexible perovskite photodetector may be addressed by separately forming an anti-reflection (AR) layer.

Hereinafter, to evaluate the flexible characteristics of the flexible perovskite X-ray detector of Example 1, it was evaluated whether an X-ray signal was distorted according to the bending radius. The results are described below with reference to FIGS. 32A to 32C.

FIG. 32A illustrates an output signal when a bending radius of a flexible perovskite X-ray detector according to an embodiment of the present invention is 6 mm, FIG. 32B illustrates an output signal when a bending radius of a flexible perovskite X-ray detector according to an embodiment of the present invention is 4 mm, and FIG. 32C illustrates an output signal when a bending radius of a flexible perovskite X-ray detector according to an embodiment of the present invention is 2 mm.

Referring to FIGS. 32A to 32C, it can be confirmed that when an X-ray signal having a time interval of 50 ms is input, there is no signal distortion in the flexible perovskite X-ray detectors that are bent according to a change in a bending radius.

This means that the flexible perovskite X-ray detector of Example 1 has excellent flexibility, and thus, an X-ray image may be obtained without distortion.

The flexible characteristics of the flexible perovskite X-ray detector of Example 1 are the same as that the scintillator and flexible perovskite photodetector of Example 1 do not exhibit signal distortion according to a change in a bending radius.

That is, it can be confirmed that the flexible perovskite X-ray detector of Example 1 includes the flexible characteristics of the scintillator and perovskite photodetector according to an embodiment.

Although the present invention has been described through limited examples and figures, the present invention is not intended to be limited to the examples. Those skilled in the art will appreciate that various modifications, additions and substitutions are possible, without departing from the scope and spirit of the invention. Therefore, it should be understood that there is no intent to limit the invention to the embodiments disclosed, rather, the invention is to cover all modifications, equivalents, and alternatives falling within the spirit and scope of the invention as defined by the claims.

DESCRIPTION OF SYMBOLS

100: perovskite X-ray detector
110: scintillator
120: perovskite photodetector
121: substrate
122: first electrode
123: hole transport layer
124: perovskite light absorption layer
125: electron transport layer
126: second electrode

The invention claimed is:

1. A self-powered perovskite X-ray detector, comprising a perovskite photodetector placed under a scintillator configured to convert incident X-rays into visible light,
the perovskite photodetector comprising:
a substrate placed under the scintillator;
a first electrode formed under the substrate;
a hole transport layer formed under the first electrode;
a perovskite light absorption layer formed under the hole transport layer;
an electron transport layer formed under the perovskite light absorption layer; and
a second electrode formed under the electron transport layer,
wherein the scintillator and the perovskite light absorption layer comprise a perovskite compound represented by Formula 1 below:

  [Formula 1]

where A is a monovalent cation, M is a divalent metal cation or a trivalent metal cation, X is a monovalent anion, a+2b=c when M is a divalent metal cation, a+3b=4c when M is a trivalent metal cation, and a, b, and c are natural numbers, and
wherein the substrate of the perovskite photodetector contacts the scintillator.

2. The self-powered perovskite X-ray detector according to claim 1, wherein the perovskite X-ray detector is a flexible device or a non-flexible device.

3. The self-powered perovskite X-ray detector according to claim 2, wherein the scintillator comprises at least one of polydimethylsiloxane (PDMS), polyethylene terephthalate (PET), polyethylene naphthalene (PEN), polyimide (PI), triacetyl cellulose (TAC), polyacryl (PA), polyurethane (PU), polyphenylene sulfide (PPS), polyarylate, polycarbonate (PC), and cellulose acetate propionate (CAP).

4. The self-powered perovskite X-ray detector according to claim 1, wherein the perovskite compound comprised in the scintillator is a nanocrystal.

5. The self-powered perovskite X-ray detector according to claim 1, wherein the monovalent cation is at least one selected from the group consisting of a $C_{1-24}$ linear or branched alkyl group, an amine group ($-NH_3$), a hydroxyl group ($-OH$), a cyano group ($-CN$), a halogen group, a nitro group ($-NO$), a methoxy group ($-OCH_3$) or an imidazolium group-substituted $C_{1-24}$ linear or branched alkyl group, $Li^+$, $Na^+$, $K^+$, $Rb^+$, $Cs^+$, $Fr^+$, Cu $(I)^+$, Ag $(I)^+$ and Au $(I)^+$.

6. The self-powered perovskite X-ray detector according to claim 1, wherein the divalent metal cation comprises at least one selected from the group consisting of $Pb^{2+}$, $Sn^{2+}$, $Ge^{2+}$, $Cu^{2+}$, $Co^{2+}$, $Ni^{2+}$, $Ti^{2+}$, $Zr^{2+}$, $Hf^{2+}$ and $Rf^{2+}$.

7. The self-powered perovskite X-ray detector according to claim 1, wherein the trivalent metal cation comprises at least one selected from the group consisting of $In^{3+}$, $Bi^{3+}$, $Co^{3+}$, $Sb^{3+}$, $Ni^{3+}$, $Al^{3+}$, $Ga^{3+}$, $Tl^{3+}$, $Sc^{3+}$, $Y^{3+}$, $La^{3+}$, $Ce^{3+}$, $Fe^{3+}$, $Ru^{3+}$, $Cr^{3+}$, $V^{3+}$ and $Ti^{3+}$.

8. The self-powered perovskite X-ray detector according to claim 1, wherein the monovalent anion comprises at least one selected from the group consisting of $F^-$, $Cl^-$, $Br^-$, $I^-$, $SCN^-$, $BF_4^-$ and $PF_6^-$.

9. The self-powered perovskite X-ray detector according to claim 1, wherein the scintillator has a transient photoluminescence (transient PL) average lifespan of 0.1 ns to 1000 ns.

10. The self-powered perovskite X-ray detector according to claim 1, wherein the scintillator has a thickness of 1 μm to 1.5 mm.

11. The self-powered perovskite X-ray detector according to claim 1, wherein the perovskite light absorption layer has a thickness of 10 nm to 200 μm.

12. The self-powered perovskite X-ray detector according to claim 1, wherein the perovskite photodetector has a responsivity (R) of 0.0001 A/W to 1 A/W.

13. The self-powered perovskite X-ray detector according to claim 1, wherein the perovskite photodetector has a specific detectivity (D*) of $10^9$ cmHz$^{0.5}$/W to $10^{13}$ cmHz$^{0.5}$/W.

14. The self-powered perovskite X-ray detector according to claim 1, wherein the perovskite photodetector has a reaction time of 0.01 μs to 100 μs.

15. The self-powered perovskite X-ray detector according to claim 1, wherein the perovskite X-ray detector has a current density of 0.00001 mA/cm² to 10 mA/cm².

16. The self-powered perovskite X-ray detector according to claim 1, wherein an X-ray sensitivity of the perovskite X-ray detector is 10 μCmGy$_{air}^{-1}$ cm$^{-2}$ to 1,000 μCmGy$_{air}^{-1}$ cm$^{-2}$ based on an area of an active region.

17. The self-powered perovskite X-ray detector according to claim 1, wherein an X-ray sensitivity of the perovskite X-ray detector is 100 $\mu CmGy_{air}^{-1}$ $cm^{-3}$ to 1,000 $\mu CmGy_{air}^{-1}$ $cm^{-3}$ based on a volume of an active region.

* * * * *